United States Patent [19]

Sakakibara et al.

[11] 4,242,504
[45] Dec. 30, 1980

[54] 3″-ACYLATED MACROLIDE ANTIBIOTICS

[75] Inventors: Hideo Sakakibara, Mishima; Osamu Okegawa, Shizuoka; Toshiyuki Watanabe, Shizuoka; Tatsuro Fujiwara, Shizuoka; Susumu Watanabe, Shizuoka; Satoshi Omura, Tokyo; Tetsuo Matsuda, Shizuoka, all of Japan

[73] Assignee: Toyo Jozo Kabushiki Kaisha, Shizuoka, Japan

[21] Appl. No.: 37,859

[22] Filed: May 10, 1979

[30] Foreign Application Priority Data

May 10, 1978 [JP] Japan .................................. 53-55876
Apr. 12, 1979 [JP] Japan .................................. 54-44590

[51] Int. Cl.³ ............................................ C07H 17/08
[52] U.S. Cl. .................................. 536/17 R; 424/180
[58] Field of Search ........................ 536/17, 9; 424/180

[56] References Cited

U.S. PATENT DOCUMENTS 4,017,607  4/1977  Inouye et al. .......................... 536/17

FOREIGN PATENT DOCUMENTS 2835547  2/1979  Fed. Rep. of Germany ............. 536/17
48-8022484  3/1973  Japan ................................... 536/17

OTHER PUBLICATIONS

Inouye et al., Chemical Abstracts, 89, 60030g, 1978.

Primary Examiner—Johnnie R. Brown
Assistant Examiner—Blondel Hazel
Attorney, Agent, or Firm—Young & Thompson

[57] ABSTRACT

3″-acylated macrolide antibiotics of the formula

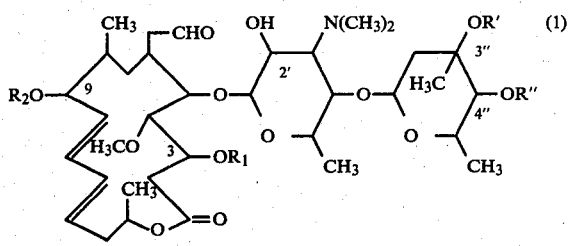

wherein $R_1$ is hydrogen or $C_{2-3}$ alkanoyl, $R_2$ is hydrogen or $C_{2-4}$ alkanoyl, at least one of $R_1$ and $R_2$ being hydrogen, and one of R′ and R″ being $R_3$ and the other $R_4$, $R_3$ being $C_{2-6}$ alkanoyl and $R_4$ being $C_{2-5}$ alkanoyl, or a pharmaceutically acceptable salt thereof.

15 Claims, No Drawings

3"-ACYLATED MACROLIDE ANTIBIOTICS

This invention relates to novel 3"-acylated macrolide antibiotics. More particularly this invention relates to compounds of the formula

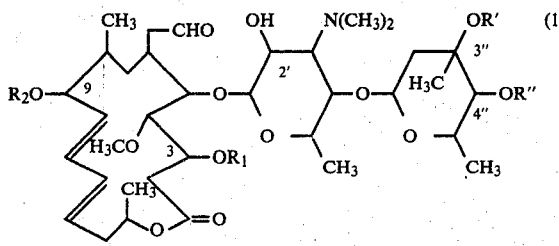

wherein $R_1$ is hydrogen or $C_{2-3}$ alkanoyl, $R_2$ is hydrogen or $C_{2-4}$ alkanoyl, at least one of $R_1$ and $R_2$ being hydrogen, and one of $R'$ and $R''$ being $R_3$ and the other $R_4$, $R_3$ being $C_{2-6}$ alkanoyl and $R_4$ being $C_{2-5}$ alkanoyl, or a pharmaceutically acceptable salt thereof.

Preferable examples of the salt are inorganic salts such as hydrochloride, sulfate or phosphate, or organic salts such as acetate, propionate, tartrate, citrate, succinate, malate, aspartate or glutamate. Other non-toxic salts can also be used.

The novel compound [1] has enhanced antibacterial activities against susceptible or resistant strains as compared with priora known 16-membered macrolide antibiotics such as leucomycin group antibiotics including josamycin, SF-837 group antibiotics, YL-704 group antibiotics and espinomycin group antibiotics. Especially the novel compounds are effective against the strains resistant to other macrolide antibiotics such as oleandomycin, erythromycin, carbomycin and spiramycin. Moreover, deacylation at the 4" position, which results in inactivation of 16-membered macrolide antibiotics, cannot easily occur, and hence the sustained blood level is increased. Furthermore, the strong continuous bitter taste generally characteristic of macrolide antibiotics is decreased, and hence syrups for infants, who can not be administered tablets or capsules can be prepared. The antibiotics [1] of the present invention show excellent clinical infectious therapeutic effects.

Compounds [1] of the present invention are influenced by a substituent at position 3 or substituents at positions 3" and 4" of the formula [1]. Therefore when position 3" is acylated and if the original acyl group at the 4" position is not rearranged to position 3" as by an acyl rearrangement, i.e. in the case of a compound of the formula [1']

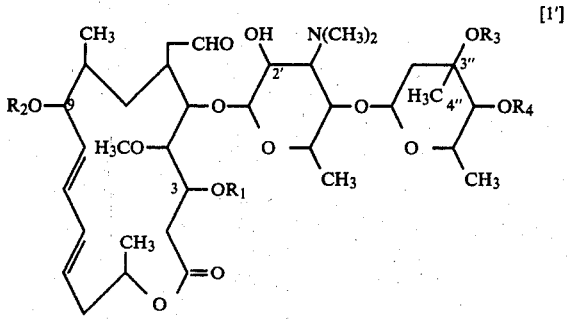

wherein $R_3$ is $C_{2-6}$ alkanoyl, $R_4$ is $C_{2-5}$ alkanoyl, and $R_1$ and $R_2$ have the same meanings hereinbefore, the nomenclature is based on the starting material which is a known antibiotic of formula [2] hereinbelow. When the original acyl group at position 4" is rearranged to position 3" as by an acyl rearrangement, i.e. in the case of a compound of the formula [1"]

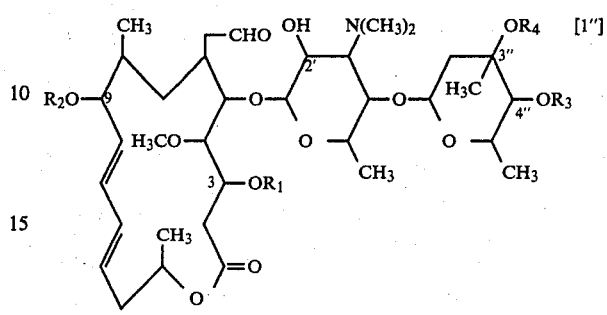

wherein $R_1$, $R_2$, $R_3$ and $R_4$ have the same meanings hereinbefore, the nomenclature is based on that of leucomycin U, an anti-biotic of formula [2] hereinbelow wherein $R_1$ is acetyl and $R_4$ is hydrogen, and leucomycin V, an antibiotic of formula [2] hereinbelow wherein $R_1$ and $R_4$ are hydrogen [Japanese Patent Publication No. 48-4555 and "Progress in Antimicrobial and Anticancer Chemotherapy", Vol. II, 1043–1049 (1970)].

The said known antibiotic is expressed by the following formula

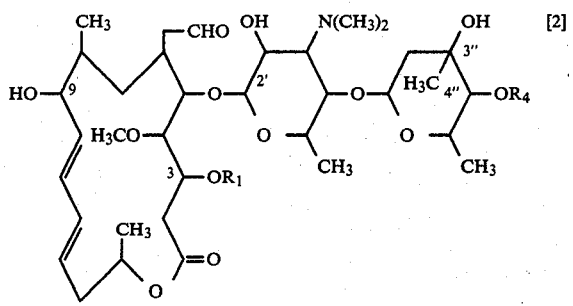

wherein $R_1$ and $R_4$ have the same meanings hereinbefore, and includes the following antibiotics:

| Antibiotics | $R_1$ | $R_4$ |
| --- | --- | --- |
| Leucomycin $A_1$ | H | $COCH_2CH(CH_3)_2$ |
| Leucomycin $A_5$ | H | $COCH_2CH_2CH_3$ |
| Leucomycin $A_7$ | H | $COCH_2CH_3$ |
| Leucomycin $A_9$ | H | $COCH_3$ |
| Leucomycin $A_3$ | $COCH_3$ | $COCH_2CH(CH_3)_2$ |
| Josamycin (Leucomycin $A_3$) | $COCH_3$ | $COCH_2CH(CH_3)_2$ |
| YL-704 $A_4$ | $COCH_3$ | $COCH_2CH(CH_3)_2$ |
| Leucomycin $A_4$ | $COCH_3$ | $COCH_2CH_2CH_3$ |
| Leucomycin $A_6$ | $COCH_3$ | $COCH_2CH_3$ |
| YL-704 $B_3$ | $COCH_3$ | $COCH_2CH_3$ |
| Leucomycin $A_8$ | $COCH_3$ | $COCH_3$ |
| YL-704 $A_1$ | $COC_2H_5$ | $COCH_2CH(CH_3)_2$ |
| SF-837 $A_2$ | $COC_2H_5$ | $COCH_2CH_2CH_3$ |
| Espinomycin $A_2$ | $COC_2H_5$ | $COCH(CH_3)_2$ |
| SF-837 | $COC_2H_5$ | $COCH_2CH_3$ |
| SF-837 $A_1$ | $COC_2H_5$ | $COCH_2Ch_3$ |
| YL-704 $B_1$ | $COC_2H_5$ | $COCH_2CH_3$ |
| Espinomycin $A_1$ | $COC_2H_5$ | $COCH_2CH_3$ |
| YL-704 $C_2$ | $COC_2H_5$ | $COCH_3$ |
| Espinomycin $A_3$ | $COC_2H_5$ | $COCH_3$ |

The antibiotic of formula [2] wherein $R_1$ is hydrogen, has four hydroxyl groups at positions 3, 9, 2' and 3", and in the case that $R_1$ is acetyl or propionyl, the said antibiotic has three hydroxyl groups at positions 9, 2' and 3". In these groups, the hydroxyl groups at positions 3, 9 and 2' are easily acylated and hence many acylated derivatives thereof have been reported. However, a hydroxyl group at position 3" has been reported to be inactive.

Recently, the acylated derivatives of hydroxyl group at position 3" were reported [Japanese Patents Open No. 49-124087 and No. 51-26887]. These compounds thus reported have initially a propionyl group at position 3 and an acyl group at position 9. In order to produce the acyl derivatives at position 3" (hereinafter referred to as 3"-acyl derivatives, etc.) having at least one hydroxyl group at positions 3 and 9, especially introducing the acyl group to position 3" alone in the known antibiotics hereinabove has been practically impossible by the known acylation methods due to the presence of the highly reactive hydroxyl groups at the positions other than 3".

We have found that a hydroxyl group at a position other than 3", especially a hydroxyl group at position 3 and/or 9, can be protected by a protective group which can easily be removed without incurring 3"-deacylation after prior acylation of a hydroxyl group at position 3".

An object of the present invention is to provide a novel antibiotic expressed by the formula [1] hereinbefore.

Another object of the present invention is to provide novel antibiotics having higher blood level when administered and having higher activities against susceptible and resistant strains.

A further object of the present invention is to provide novel antibiotics having less bitter taste.

The compound [1] of the present invention can be produced by the following processes:

Process [A]: A compound [1'] wherein $R_1$ is $C_{2-3}$ alkanoyl and $R_2$ is hydrogen, i.e., a compound of the formula

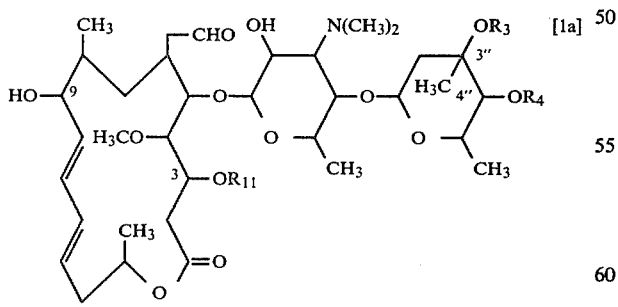

wherein $R_{11}$ is $C_{2-3}$ alkanoyl and $R_3$ and $R_4$ having the same meanings hereinbefore:

The above compound [1a] is produced by the following method:

A compound of the formula

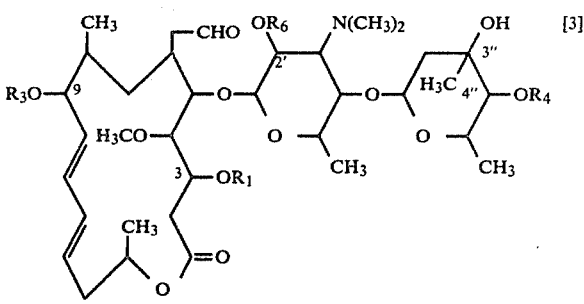

wherein $R_5$ is halogenated acetyl, p-nitrobenzoyl or silyl, $R_6$ is hydrogen or $R_{61}$, which $R_{61}$ is $C_{2-4}$ alkanoyl and $R_1$ and $R_4$ have the same meanings hereinbefore, is acylated with a $C_{2-6}$ aliphatic carboxylic acid halide under heating in the presence of an inert organic solvent and a tertiary organic amine to obtain a mixture of a compound of the formula

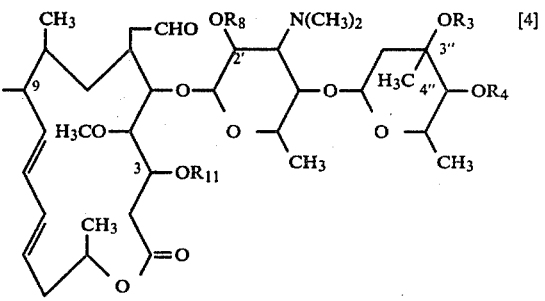

wherein $R_8$ is $R_{61}$ or $R_3$, and $R_{11}$, $R_3$, $R_4$, $R_5$ and $R_{61}$ have the same meanings hereinbefore, and a compound of the formula

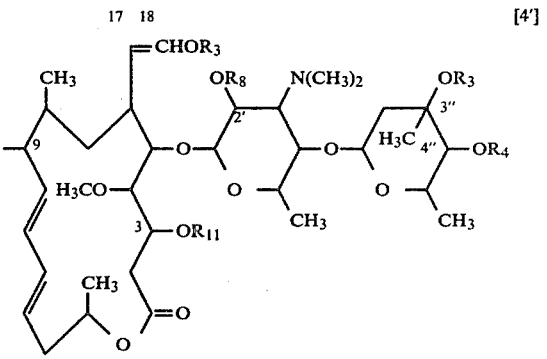

wherein $R_{11}$, $R_3$, $R_4$, $R_5$ and $R_8$ have the same meanings hereinbefore. The said mixture is treated, when $R_5$ is halogenated acetyl or p-nitrobenzoyl, with ammonia in methanol or ethanol to remove the protective group at position 9, then treated by heating in methanol to remove the acyl group at position 2'. When $R_5$ is silyl, the said mixture is treated, to remove the silyl and acyl groups at positions 18 and 2', by one of the processes of:

(a) removing the silyl and acyl groups at positions 18 and 2' by heating in aqueous lower alkanol which can contain a bask;

(b) removing the silyl and acyl groups at position 18 by treating at ambient temperature with aqueous lower alkanol in the presence of a base, thereafter removing the acyl group at position 2' by heating in methanol which can contain water;

(c) removing the acyl group at position 18 by treating with methanol containing ammonia and further removing the silyl and acyl groups at position 2' by heating in aqueous lower alcohol; or (d) removing the acyl group at position 18 by treating with methanol containing ammonia, thereafter removing the acyl group at position 2' by heating with methanol and removing the silyl group by treating with aqueous acid.

Compound [3] hereinbefore is a compound wherein is introduced the preferred protective group at position 9 of the antibiotic of formula [2] in order to prevent the acylation of the hydroxyl group at position 9 in the 3''-acylation reaction. The said protective group is a group which can be selectively removed without destroying the chemical structure after 3''-acylation, for example a halogenated acetyl group such as chloroacetyl, dichloroacetyl, trichloroacetyl or trifluoroacetyl, p-nitrobenzoyl or silyl. Among these protective groups, introducing the chlorinated acetyl group such as chloroacetyl or dichloroacetyl group was disclosed in Japanese Patent Open. No. 50-96584. Introduction of the other protective groups can be done in accordance with the methods of the said patent, i.e. reacting with carboxylic acid halide, preferably carboxylic acid chloride, in the presence of a tertiary organic amine in an inert organic solvent.

Introduction of a silyl group can be done by silylating the antibiotic of formula [2] or its 2'-acyl derivative with a suitable silylation reagent such as a tri-substituted halogeno silane or hexa-substituted silazane. An example of a trisubstituted halogenosilane is a tri-lower alkylhalogeno silane such as trimethylchlorosilane. An example of a hexa-substituted silazane is a hexa-lower alkylsilazane such as hexamethylsilazane. Any silylation reagent can be used if the introduced silyl group cannot be removed by water.

The above silylation reaction is usually carried out in an inert organic solvent such as dichloromethane, chloroform or methyl isobuty ketone, at room temperature or below. The amount of silylation reagent can be about 1-1.8 molar equivalent. In the silylation reaction with tri-substituted halogeno silane, a tertiary organic amine is preferably used as dehydrohalogenation reagent. As examples, pyridine, quinoline, N-methylmorpholine or dimethylaniline can be mentioned.

The above silylated product of formula [3] can be obtained by pouring the reaction mixture into water and extracting with a suitable water-immiscible organic solvent. The silyl group of compound [3] is stable in water and cannot be removed in the presence of water.

As hereinabove explained, in the protection of the hydroxyl group at position 9 of the antibiotic [2], a hydroxyl group at position 2' may optionally be protected by a protective group. An example of the said protective group is $C_{2-4}$ alkanoyl, preferably acetyl. 2'-acetylation can be done by the process described in Japanese Patent Publication No. 53-7434.

The above compound [3] is 3''-acylated with an aliphatic carboxylic acid halide. The reaction is carried out in the presence of a tertiary organic amine in an inert organic solvent with heating. Examples of inert organic solvents are acetone, methyl ethyl ketone, ethyl acetate, dimethoxyethane, tetrahydrofuran, dioxane, benzene or toluene. Examples of tertiary organic amines are pyridine, picoline or collidine. Other known organic amines such as triethylamine, dimethylaniline, tribenzylamine, N-methylpiperidine, Nmethylmorpholine, quinoline or isoquinoline can be used. Examples of aliphatic carboxylic acid halides are $C_{2-6}$ aliphatic carboxylic acid halides such as acetylchloride, pripionylchloride, butylylchloride, isobutylylchloride, isovalerylchloride or caproylchloride. The reaction temperature may be 50°-120° C. Reaction time can be varied depending on the reaction temperature, and since the progress can be checked by silica gel thin layer chromatography, the end point can be determined within the range of 1 to 150 hours.

In the above acylation reaction, the hydroxyl group at position 3'' is acylated and the compound having

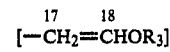

at positions 17 and 18 of

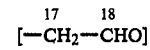

is produced as by-product. In the case of a hydroxyl group at position 3 and a previously unprotected hydroxyl group at position 2', these hydroxyl groups are also acylated. Therefore the amount of aliphatic carboxylic acid halide should be adjusted depending on the number of hydroxyl group to be acylated.

In the reaction in which the compound [3] wherein $R_1$ is hydrogen is used and a different acyl group is introduced at positions 3 and 3'' thereof, in other words in order to obtain the compound [4] wherein $R_{11}$ and $R_3$ are different acyl groups, an acyl group such as acetyl or propionyl is previously introduced in the hydroxyl group at position 3 of the above compound [3], and thereafter acylated at position 3''.

The thus-obtained mixture of compound [4] and [4''] can be isolated by adjusting the reaction mixture with alkali to pH 8-10 in water to precipitate the mixture, which is then filtered. When the reaction solvent is a water-immiscible organic solvent, the reaction mixture is poured into water, the pH is adjusted to 8-10 then material is extracted with a water-immiscible organic solvent. Further purification can be effected by chromatography using silica gel, active alumina or an adsorption resin with elution such as with benzene-acetone.

Removal of protective group at positions 9, 18 and 2'' of the mixture of compound [4] and compound [4'] depends on the protective group at position 9. In case $R_5$ is halogenated acetyl or p-nitrobenzoyl, a protective group at position 9 is removed by treating with ammonia in methanol or ethanol at room temperature. The progress of the reaction can be checked by silica gel thin layer chromatography and the reaction can be terminated when the spots of compounds [4] and [4'] have not been detected. By this reaction, a group

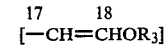

of the compound [4'] is changed to the initial

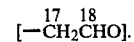

Ammonia and alcohol are distilled off from the reaction mixture to yield a compound wherein the protective groups at positions 9 and 19 are removed. The said compound is heated in methanol which can contain water to remove the acyl group at position 2'. Heating is done by refluxing with methanol. The reaction can be checked by silica gel thin layer chromatography.

In case $R_5$ is silyl, the protective groups at position 9, 18 and 2' can be removed by the following:

(A) silyl and acyl groups at positions 18 and 2' are removed by heating in aqueous lower alkanol which can contain a base;

(B) silyl and acyl groups at position 18 are removed by treating at ambient temperature in aqueous lower alkanol in the presence of a base, and an acyl group at position 2 is removed by heating in methanol which can contain water;

(C) an acyl group at position 18 is removed by treating in methanol containing ammonia, and silyl and acyl groups at position 2' are removed by heating in aqueous lower alcohol; or (D) an acyl group at position 18 is removed by treating in methanol containing ammonia, with removal of 2'-acyl group by heating in methanol and removal of a silyl group by treating with aqueous acid.

In the above, the lower alkanol is preferably methanol or ethanol. In methods (A) and (B), tertiary organic amines, alkaline carbonates or basic resins can be mentioned. Heating can be effected by refluxing the organic solvent. In (B), for example, the temperature is room temperature or below. The end point of the reaction can be checked by silica gel thin layer chromatography.

The desired comound [1a] can be obtained from the thus-prepared compound by the process hereinbelow explained.

Process [B]: A compound [1'] wherein $R_1$ is hydrogen and $R_2$ is $C_{2-4}$ alkanoyl, i.e., a compound of the formula

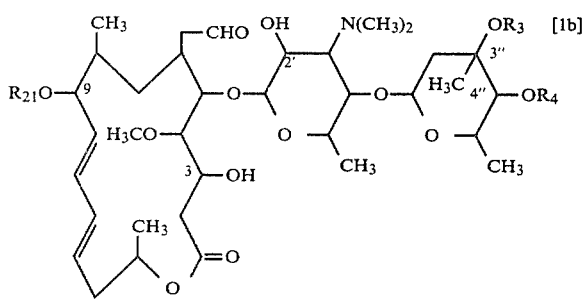

wherein $R_{21}$ is $C_{2-4}$ alkanoyl and $R_3$ and $R_4$ have the same meanings hereinbefore, can be obtained by reacting a compound of the formula

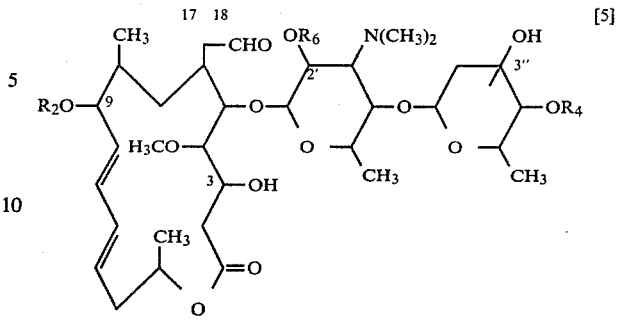

wherein $R_6$ is hydrogen or $R_{61}$, in which $R_{61}$ is $C_{2-4}$ alkanoyl and $R_2$ and $R_4$ have the same meanings hereinbefore, with $C_{2-4}$ aliphatic carboxylic acid anhydride in the presence of an inorganic base to prepare a compound of the formula

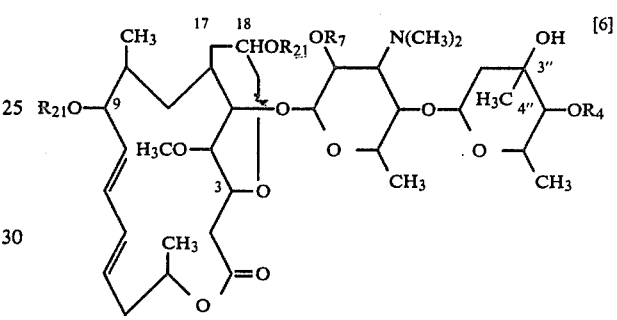

wherein $R_7$ is $R_{61}$ or $R_{21}$, and $R_{21}$, $R_4$ and $R_{61}$ have the same meanings hereinbefore, reacting compound [6] with $C_{2-6}$ aliphatic carboxylic acid halide in the presence of a tertiary organic amine in an inert organic solvent with heating to prepare a compound of the formula

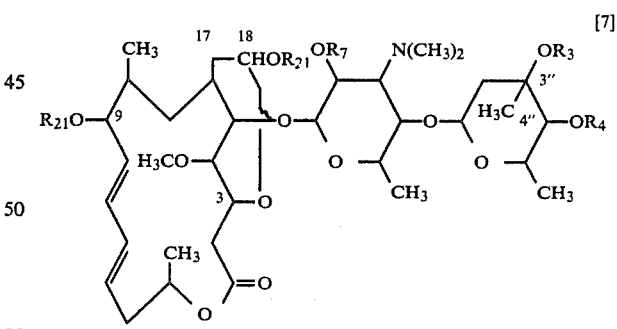

wherein $R_{21}$, $R_3$, $R_4$ and $R_7$ have the same meanings hereinbefore, and, removing the protective group at position 18 by treating with a methanol solution of ammonia or an ethanol solution of an aqueous alkaline carbonate, then removing the 2' acyl group by heating in methanol.

The above compound [5] is the antibiotic [2] wherein $R_1$ is hydrogen, such as leucomycin-$A_1$, —$A_5$, —$A_7$, —$A_9$ or an acyl derivative thereof. The acyl derivative is 9-acyl, 2'-acyl or 9,2'-diacyl.

Introduction of protective groups to positions 3 and 18 of compound [5] hereinabove is done by reacting it with a corresponding carboxylic acid anhydride in the presence of an inorganic base.

Examples of inorganic bases are alkali hydroxides such as potassium hydroxide or sodium hydroxide, alkali carbonates such as potassium carbonate or sodium carbonate, and alkali hydrogen carbonates such as sodium bicarbonate. Preferred examples are alkali carbonates and alkali hydrogen carbonates. The corresponding carboxylic acid anhydride is a $C_{2-4}$ carboxylic acid anhydride such as acetic anhydride, propionic anhydride or lactic anhydride. The temperature for introducing the protective group is 30°–100° C., preferably 40°–60° C.

When antibiotic [5] previously acylated at position 9 is used, the spot of the thin layer chromatogram of antibiotic [5] is checked; and when antibiotic [5] wherein position 9 is occupied by hydroxyl, the spot of the acylated derivative of the said hydroxyl group is checked for termination of the reaction.

By the above reaction, the aldehyde group at position 18 is acylated, and the hydroxyl group at position 3 is protected by ring closure between the carbon atom at position 18 and the oxygen atom at position 3. Also in the case that the hydroxyl group at position 9 is not acylated previously, and/or the hydroxyl group at position 2 is not acylated previously by the acyl group, which is preferably an acetyl group, these hydroxyl groups can be acylated. Since this protection of the 3 and 18 positions uses the preferred protective groups for selective reaction and is quite stable, it is a quite excellent and convenient protection for the hydroxyl group at position 3.

Separation of the product [6] from the reaction mixture can be effected by the same procedure of separation and purification as for compound [4] in the process [A] hereinbefore.

The acylation at position 3" of compound [6] can be effected by the same process of 3"-acylation as compound [3] in process [A] hereinbefore. The thus-obtained compound [7] can be isolated and purified by the same procedure as compound [4] in process [A] hereinbefore.

The removal of the protective groups at positions 3 and 18 of compound [7] can be done quantitatively by allowing the reaction medium to stand at room temperature in a methanol solution containing ammonia or an ethanol solution containing aqueous alkali carbonate. The extent of reaction can be checked by silica gel thin layer chromatography, the disappearance of the spot of compound [7] revealing the termination of the reaction.

The 2'-acyl group in the 9, 2', 3"-triacyl derivative, which can be obtained from vacuum concentration of the reaction mixture, is removed by heating in methanol which can contain water. Heating can be effected by refluxing methanol. The end point can be determined by checking the silica gel thin layer chromatogram wherein the spot of the above 9, 2', 3"-triacyl derivative cannot be detected.

The product obtained by distilling off methanol is separated and purified as hereinbelow explained to obtain compound [1b].

Process [C]: A compound [1'] wherein $R_1$ and $R_2$ are hydrogen, i.e., the compound of [1c] of the formula

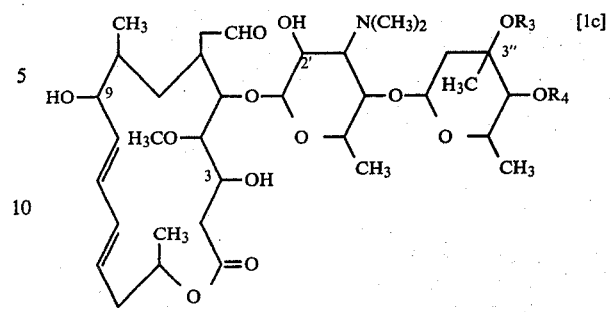

wherein $R_3$ and $R_4$ have the same meanings hereinbefore.

The above compound [1c] is prepared by reacting compound [8] of the formula wherein $R_{51}$ is a chlorinated acetyl group, $R_6$ is hydrogen or $R_{61}$ in which $R_{61}$ is $C_{2-4}$ alkanoyl, and $R_4$ has the same meanings as above, with $C_{2-4}$ aliphatic carboxylic acid anhydride in the presence of a $C_{2-4}$ inorganic acid anhydride in the presence of an inorganic base to prepare a compound [9] of the formula wherein $R_7$ is $R_{61}$ or $R_{21}$, in which $R_{21}$ is $C_{2-4}$ alkanoyl, and $R_{51}$, $R_{61}$ and $R_4$ have the same meanings hereinbefore; and acylating the compound [9] at position 3" with a $C_{2-6}$ aliphatic carboxylic acid halide in the presence of a tertiary organic amine in an inert organic solvent.

Also compound [1c] can be prepared as follows:

A 2'-acyl antibiotic [10] of the formula

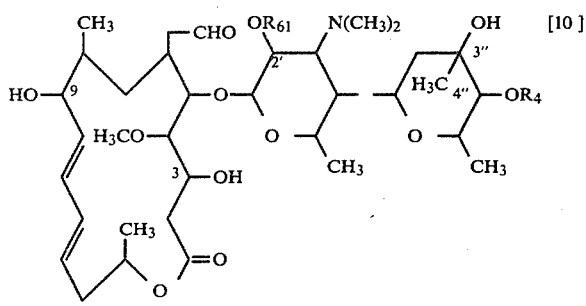

wherein $R_4$ and $R_{61}$ have the same meanings hereinbefore, is protected at positions 3 and 9 by a chlorinated acetyl halide in the presence of a tertiary organic amine in an inert organic solvent to prepare compound [11] of the formula

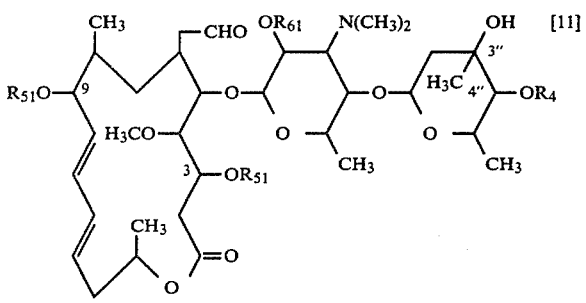

wherein $R_4$, $R_{51}$ and $R_{61}$ have the same meanings hereinbefore. Compound [11] is 3''-acylated by a $C_{2\text{-}6}$ aliphatic carboxylic acid halide in the presence of a tertiary organic amine in an inert organic solvent to obtain compound [12] of the formula

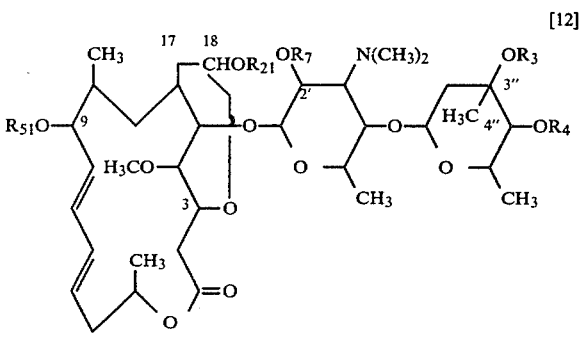

wherein $R_{21}$, $R_3$, $R_4$, $R_5$ and $R_7$ have the same meanings hereinbefore, or compound [13] of the formula

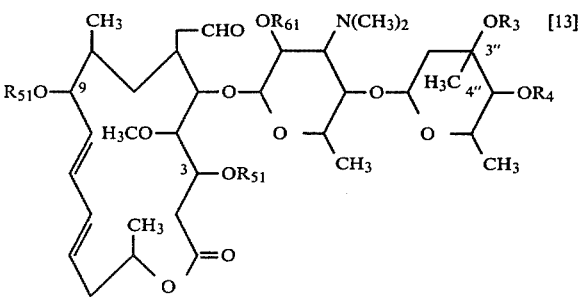

wherein $R_3$, $R_4$, $R_{51}$ and $R_{61}$ have the same meanings hereinbefore.

Compound [12] or [13] is treated with ammonia in methanol or ethanol to obtain compound [14] of the formula

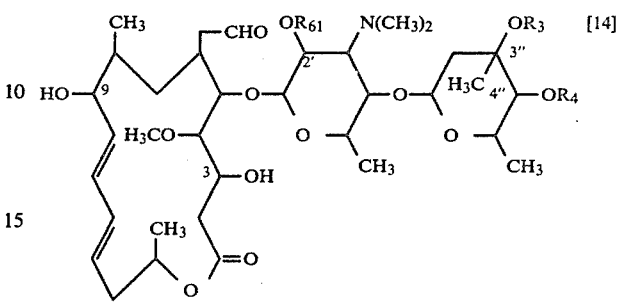

wherein $R_3$, $R_4$ and $R_6$ have the same meanings hereinbefore, and compound [14] is heated in methanol which can contain water to remove the acyl group at position 2'.

The above compound [8] is the antibiotic [2] in which is introduced at first the protective group for the hydroxyl group at position 9 for preventing the acylation of the hydroxyl groups at posinions 3 and 9 in the forthcoming 3''-acylation reaction. The said protective group is a group which can be easily removed without destroying the chemical structure upon post-3''-acylation, and is preferably a chlorinated acetyl group such as chloroacetyl, dichloroacetyl or trichloroacetyl.

These 9-protected compounds can, if required, be previously or subsequently protected as to the hydroxyl group at position 2'. The preferred example is a $C_{2\text{-}4}$ alkanoyl group such as acetyl.

Then the hydroxyl group at position 3 of compound [8] is protected by reacting with the corresponding carboxylic acid anhydride, preferably acetic anhydride, in the presence of the inorganic base to protect positions 3 and 18. Introduction can be effected by the same procedure as in process [B] hereinbefore. Disappearance of the spot of compound [8] on the silica gel thin layer chromatogram reveals the end point of the reaction. Compound [9] can be obtained by the same procedure as the isolation procedure of process [A].

In this process, compound [11] can be used instead of compound [4] to obtain compound (1c].

Compound [11] is a compound in which is introduced the protective group for the hydroxyl group at positions 3 and 9 for preventing acylation in the forthcoming 3''-acylation. The hydroxyl group at the 2'-position is preferably protected by the other protective group. A preferred example is the acetyl group. Hydroxyl groups at positions 3 and 9 of the 2'-acylated antibiotic [10] are protected by suitable protective groups. Preferred examples are chlorinated acetyl groups such as chloroacetyl, dichloroacetyl or trichloroacetyl. Introduction of the protective gropu is performed with a 2-3 times excess amount of chlorinated acetyl halide.

Isolation of compound [4] in process [A] can be applied for obtaining compound [12] or [13] by 3''-acylation of compound [9] or [11].

The removal of the protective groups at positions 9, 3 and 18 of compound [12] or at position 3 or 9 of compound [13] can be achieved by treating with a methanol or ethanol solution containing ammonia. The reaction can proceed at room temperature. The end point of the reaction can be checked by disappearance of compound [12] or [13] on a silica gel thin layer chromatogram.

Compound [14] obtained by distilling off ammonia and methanol from the reaction mixture is heated in methanol which can contain water, to remove the 2'-acetyl group. Heating is by refluxing methanol. The product obtained by distilling the methanol can be purified to prepare compound [1c].

Further, compound [1c] can be preferred by the following process:

A compound [21] of the formula

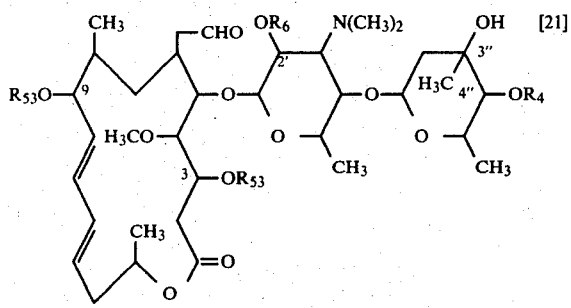

wherein $R_{53}$ is silyl, and $R_4$ and $R_6$ have the same meanings hereinbefore, is acylated with $C_{2-6}$ aliphatic carboxylic acid halide while heating in an inert organic solvent to prepare a mixture of compound [22] of the formula

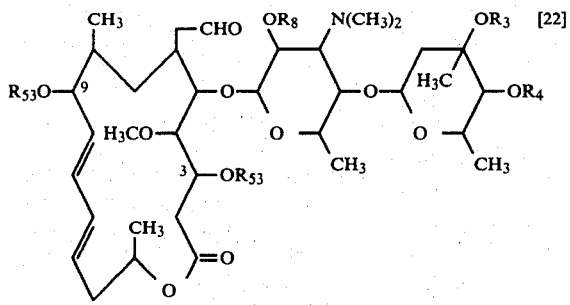

wherein $R_8$ is $R_6$ or $R_3$, and $R_3$, $R_4$, $R_{53}$ and $R_{61}$ have the same meanings hereinbefore, and compound [22'] of the formula

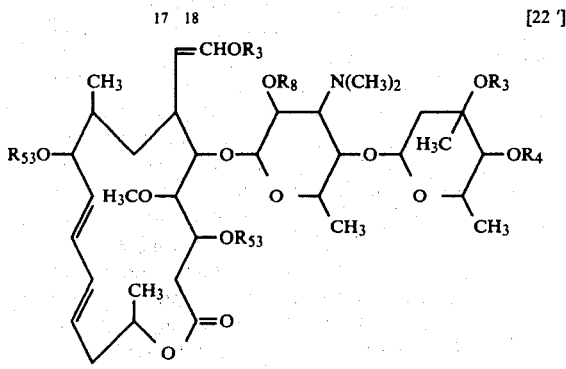

wherein $R_3$, $R_4$, $R_{53}$ and $R_8$ have the same meanings hereinbefore.

The mixture is treated as follows:

(A) removing the silyl and acyl groups at positions 18 and 2' by heating in aqueous lower alkanol which can contain a base;

(B) removing the silyl and acyl groups at position 18 by treating at ambient temperature in aqueous lower alkanol in thk presence of a base, and removing the 2'-acyl group by heating in methanol which can contain water;

(C) removing the acyl group at position 18 by treating with methanol containing ammonia, thereafter removing the silyl and 2'-acyl groups by heating with aqueous lower alcohol; or (D) removing the acyl group at position 18 by treating with methanol containing ammonia, thereafter removing the 2'-acyl group by heating with methanol and removing the silyl group by treating with aqueous acid.

Compound [21] can be prepared by the same process as compound [3], wherein $R_5$ is silyl, in process [A] hereinbefore, and the amount of silylating reagent is preferably in 2-5 molar excess of the antibiotic [2] or its 2'-acyl derivative.

Compounds [22] and 22'] preparkd by 3''-acylation of compound [21] can be obtained by the same process for preparing a mixture of compounds [4] and [4'] by acylating at position 3'' of compound [3] as described in process [A] hereinbefore.

Further, removal of the silyl and 18- and 2'-acyl groups of the mixture of the compounds [22] and [22'] can be achieved by the same process as in process [A] hereinbefore, wherein are removed the silyl and 18- and 2'-acyl groups of the mixture of compounds [4] and [4'] in which $R_5$ is silyl.

Process [D]: A compound [1''] wherein $R_1$ is $C_{2-3}$ alkanoyl and $R_2$ is hydrogen, i.e., compound [1d] of the formula

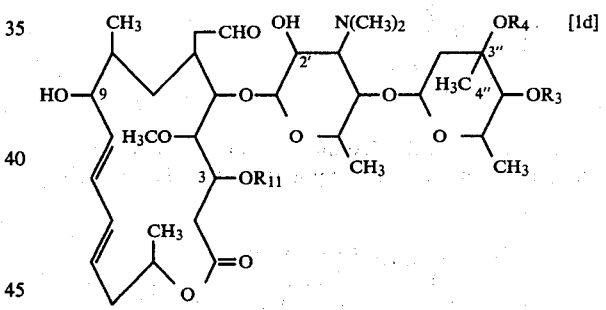

wherein $R_{11}$ is $C_{2-3}$ alkanoyl, and $R_3$ and $R_4$ have the same meanings hereinbefore.

The above compound [1d] can be prepared as follows:

2'-acyl antibiotic [15] of the formula

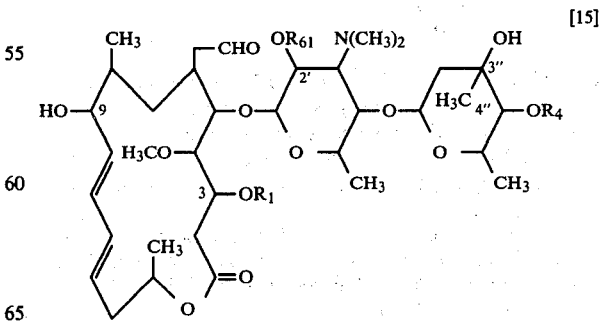

wherein $R_{61}$ is $C_{2-4}$ alkanoyl, and $R_1$ and $R_4$ have the same meanings hereinbefore, is reacted with a p-nitrobenzoyl halide in the presence of a tertiary organic amine in an inert organic solvent to prepare compound [16] of the formula

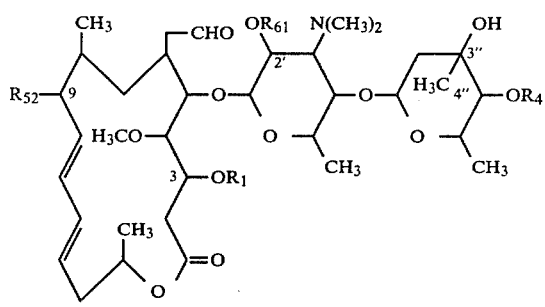

wherein $R_{52}$ is p-nitrobenzoyl, and $R_1$, $R_4$ and $R_{61}$ have the same meanings hereinbefore, and compound [16] is acylated by heating with a $C_{2-6}$ aliphatic carboxylic acid anhydride in the presence of an alkali carbonate or a tertiary organic base to prepare a mixture of compound [17] of the formula

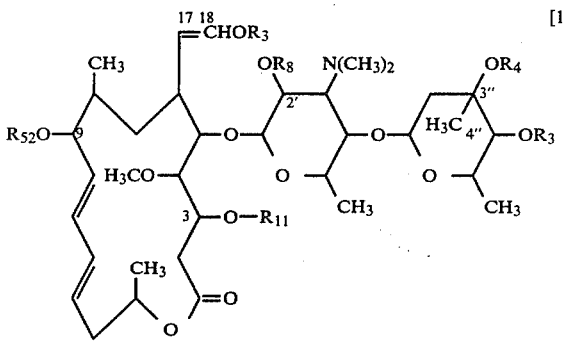

wherein $R_{11}$, $R_3$, $R_4$, $R_{52}$ and $R_8$ have the same meanings hereinbefore, and compound [18] of the formula

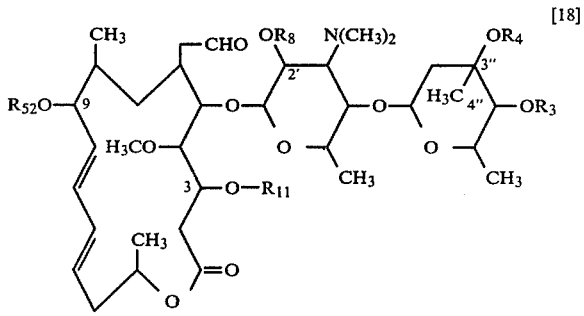

wherein $R_{11}$, $R_3$, $R_4$, $R_{52}$ and $R_8$ have the same meanings hereinbefore. The said mixture is treated with ammonia in ethanol to remove the protective group at position 9 and the acyl group at position 18, then heated in methanol, which can contain water, to remove the 2'-acyl group.

The above 2'-acyl antibiotic [15] can be prepared by a known method such as the process disclosed in Japanese Patent Publication No. 53-7434 and J. Med. Chem., 20 (5), 732–736 (1977).

Protection of the hydroxyl group at position 9 of the 2'-acyl antibiotic [15] can be achieved by reacting with a p-nitrobenzoyl halide, preferably p-nitrobenzoylchloride, in the presence of a tertiary organic amine in an inert organic solvent. Examples of inert organic solvents are acetone, methyl ethyl ketone, dichloromethane, ethyl acetate, dimethoxyethane, tetrahydrofuran and dioxane. Examples of tertiary organic amines are pyridine, picoline or collidine, or any other known tertiary organic amine can be used. The above reaction proceeds under ice-cooling or at room temperature.

If a chlorinated acetyl group such as monochloroacetyl or dichloroacetyl is used in place of p-nitrobenzoyl as the protective group for position 9, the acyl group at position 3 will simultaneously be removed upon the removal of the said protective group in the forthcoming process; therefore, p-nitrobenzoyl is preferable for the protectivk group at position 9.

The thus-produced compound [16] can be obtained by separating, in the case of a water-miscible organic solvent of the reaction medium, the precipitate by filtration while adjusting the medium to pH 8–10. Or the compound can be obtained by extracting, in the case of a water-immiscible organic solvent of the reaction medium, with a water-immiscible organic solvent after pouring the reaction mixture into water and adjusting the same to pH 8–10. Further purification can be achieved, if required, by chromatography using for example silica gel, alumina or an adsorption resin.

For introduction of a different acyl group to positions 3 and 3" of compound [15], wherein $R_1$ is hydrogen, namely in case of obtaining compounds [17] and [18] wherein $R_{11}$ and $R_3$ are different acyl groups, the desired acyl group such as acetyl or propionyl is previously introduced in the hydroxyl group at position 3 of compound [16].

Further, acylation of compound [16] with the corresponding aliphatic carboxylic acid anhydride is achieved by heating in the presence of a base. Examples of the base are alkali carbonates such as potassium carbonate or sodium carbonate, and tertiary organic amines such as pyridine, picoline or collidine. Known tertiary organic amines other than the pyridine group can be used. The reaction temperature may usually be 50°–120° C., preferably 80°–100° C. The reaction time can be varied depending on the reaction temperature, since the progress of the reaction can be checked by silica gel thin layer chromatography, the disappearance of a spot of compound [16] on the chromatogram revealing the end point of the reaction, usually at 1–100 hours.

As a result of the above reaction, the original 4"-acyl group is rearranged to position 3", and the $C_{2-6}$ alkanoyl group, namely acetyl or propionyl, is introduced at position 4". Further, in the case of 2'-acyl antibiotic [15], wherein $R_1$ is hydrogen, the hydroxyl group at position 3 is acylated. Furthermore, the aldehyde group at position 18 is acylated to a substantial extent, and hence the compounds [17] and [18] are prepared.

The thus-prepared mixture of compounds [17] and [18] can be separately purified, if required. However, the mixture itself can be used for the following reaction:

Next, removal of the protective group at position 9 of compounds [17] and [18] can be achieved by treating with ammonia in methanol or ethanol at room temperature. By this reaction, the acyl group at position 18 of compound [17] is removed. The end point of the reaction can be checked by silica gel thin layer chromatography, and so can be determined by the disappearance of a spot corresponding to compounds [17] and [18] on a thin layer chromatogram.

The compound, wherein the protective group for position 9 has been removed, is obtained by distilling of ammonia and alcohol from the reaction mixture, and the removal of the 2'-acyl group of the compound is achieved by heating to reflux with methanol, which can contain water.

The product [1d] can be obtained by distilling off methanol and purifying.

Process [E]: A compound [1''] wherein $R_1$ is hydrogen and $R_2$ is $C_{2-4}$ alkanoyl, i.e., compound [1e] of the formula

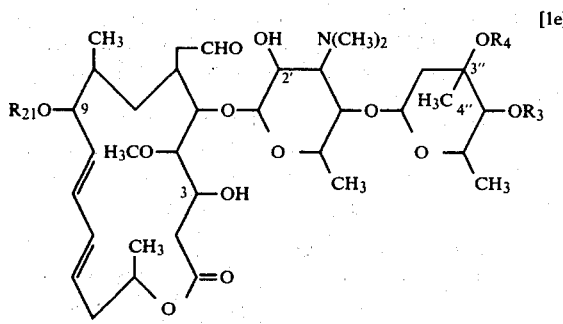

wherein $R_{21}$ is $C_{2-4}$ alkanoyl, and $R_3$ and $R_4$ have the same meanings as hereinbefore.

The above compound [1e] is prepared by reacting compound [5] with a $C_{2-4}$ aliphatic carboxylic acid anhydride in the presence of an inorganic base to prepare compound [6], acylating compound [6] with a $C_{2-6}$ aliphatic carboxylic acid anhydride by heating in the presence of an alkali carbonate or a tertiary organic amine to prepare compound [19] of the formula

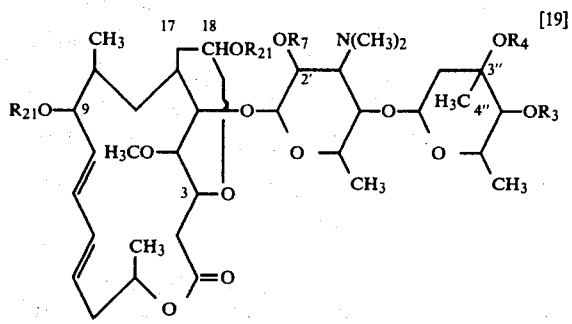

wherein $R_{21}$, $R_3$, $R_4$ and $R_7$ have the same meanings hereinbefore, and removing the protective group at position 18 of compounds [19] by treating with ammonia in methanol or aqueous alkali carbonate in ethanol, then removing the 2'-acyl group by heating with methanol.

The preparation of compounds [5] and [6] hereinabove is illustrated in process [B] hereinbefore.

Acylation of compound [6] by the corresponding carboxylic acid anhydride for preparing compound [19] can be achieved by the same process for preparing compounds [17] and [18] from compound [16] illustrated in process [D] hereinabove.

The removal of the protective groups at positions 3 and 18 of compound [19] can be achieved by treating compound [19] with methanol containing ammonia or ethanol containing aqueous alkali carbonate at room temperature or with heating if required. By this reaction, the acyl group at position 18 is removed to form the original aldehyde group. The reaction can be traced by checking the disappearance of a spot corresponding to compound [19] on a silica gel thin layer chromatogram.

The 9, 2', 3''-triacyl derivative thereof, which can be obtained by distilling off ammonia and methanol or ethanol from the reaction mixture, is treated by the same procedure as process [D], in which deacylation at postion 2' is performed by heating with methanol (which can contain water), to remove the 2'-acyl group. After distilling off methanol, and purifying, compound [1e] can be prepared.

Process [F]: A compound [1''] wherein $R_1$ and $R_2$ are hydrogen, i.e., a compound [1f] of the formula

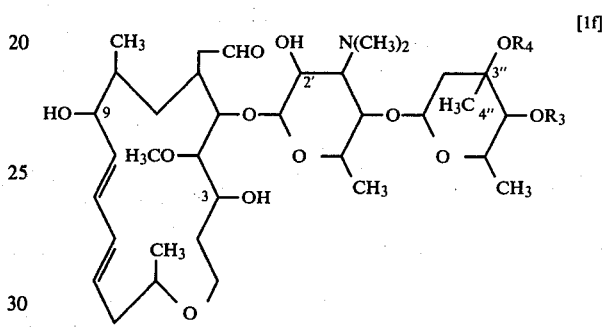

wherein $R_3$ and $R_4$ have the same meanings hereinbefore.

Compound [1f] is produced by reacting compound [8] with a $C_{2-4}$ aliphatic carboxylic acid anhydride in the presence of an inorganic base to prepare compound [9], acylating the said compound [9] by heating with a $C_{2-6}$ aliphatic carboxylic acid anhydride in the presence of an alkali carbonate or a tertiary organic amine to prepare the compound [20] of the formula

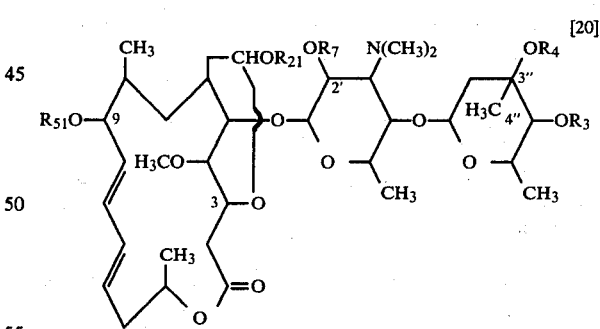

wherein $R_{51}$ is chlorinated acetyl, $R_7$ is $R_{61}$ or $R_{21}$, and $R_{21}$, $R_{61}$, $R_3$ and $R_4$ have the same meanings hereinbefore, removing the protective groups at positions 3, 9 and 18 by treating with ammonia in methanol, then removing the 2'-acyl group by heating with methanol.

The production process of compounds [8] and [9] is illustrated in process [C] hereinbefore.

Acylation of compound [9] with carboxylic acid anhydride for the preparation of compound [20] can be achieved by the same procedure for preparing compounds [17] and [18] from compound [16] as in process [D].

Removal of the protective groups at position 9 and at positions 3 and 18 can be achieved by treating compound [20] with ammonia in methanol at room temperature. By this reaction, the acyl group at position 18 is removed and changed to the original aldehyde group. Progress of the reaction is checked by disappearance of a spot corresponding to compound [20] on a silica gel thin layer chromatogram.

The 2′,3″-diacyl derivative, obtained by distilling off the ammonia and methanol from the reaction mixture, is heated in methanol (which can contain water) by the same procedure of 2′-deacylation in process [D] hereinbefore to remove the acyl group at position 2′. The product obtained by distilling off methanol is separated and purified to obtain product [1f].

Separation of compound [1] from the reaction mixture is performed in accordance with known separation and purification methods for macrolide antibiotics, such as concentration, extraction, washing, transferred extraction and recrystallization, and chromatography using silica gel, active alumina, adsorption resins or ion-exchange resins.

The antimicrobial activities of compound [1] of the present invention are shown in the following table. These data show that compound [1] of the present invention exhibits enhanced antimicrobial activity against not only the susceptible strains but also the resistant strains as compared with the known antibiotics.

der (9.82 g) of 3,2′,3″-triacetyl-9-dichloroacetyl-leucomycin $A_5$ ($Rf_B=0.62$, $Rf_C=0.35$) as a main component.

This powder was dissolved in ammonia-saturated methanol solution (300 ml), allowed to stand for one hour at room temperature and dried in vacuo to obtain a powder of 3,2′,3″-triacetyl leucomycin $A_5$ ($Rf_A=0.67$, $Rf_B=0.27$, $Rf_C=0.09$) as a main component.

The powder was dissolved in methanol (300 ml), refluxed for 20 hours and concentrated in vacuo. The residue was chromatographed on a silica gel column by eluting with benzene:acetone (7:1). Fractions showing $Rf_A=0.58$ were collected and concentrated in vacuo to obtain thk product (875 mg).

$Rf_A=0.58$, $Rf_B=0.15$

Mass (m/e): 855 ($M^+$), 796 ($M^+ -59$), 768 ($M^+ -87$).

NMR (CDCl$_3$, 100 MHz): 1.43 (3″-position: CH$_3$), 2.02 (3″-position: OAc), 2.29 (3-position: OAc), 9.79 (CHO) ppm.

The above 9-dichloroacetyl leucomycin $A_5$ was prepared by the process described in Japanese Patent Open. No. 50-96584.

EXAMPLE 2

3″-acetyl leucomycin $A_3$:

To 2′-acetyl leucomycin $A_3$ (2 g) dissolved in dry dichloromethane (10 ml) was added dry pyridine (0.7 ml) and dichloroacetylchloride (0.7 ml) with stirring under ice-cooling, for one hour at room temperature.

| Test Organisms | Minimum Inhibitory Concentration (MIC) μg/ml substance | | | | | | | | |
|---|---|---|---|---|---|---|---|---|---|
| | 3″-acetyl LM**-$A_5$ | 3″-propionyl LM-$A_5$ | 3″butylyl LM-$A_5$ | 3,3″-diacetyl LM-$A_5$ | 9,3″-diacetyl LM-$A_5$ | 3″-acetyl LM-$A_5$ | 4″-acetyl-3″-butylyl LM-$A_5$ | LM-$A_5$ | LM-$A_3$ |
| Staph.aureus 6538P | 1.6 | 0.8 | 0.8 | 1.6 | 0.8 | 1.6 | 1.6 | 1.6 | 3.1 |
| Staph.aureus MS353 | 1.6 | 1.6 | 1.6 | 1.6 | 1.6 | 1.6 | 1.6 | 1.6 | 3.1 |
| Staph.aureus MS353 C36 | 0.4 | 0.8 | 0.4 | 0.8 | 0.8 | 1.6 | 0.8 | 1.6 | 1.6 |
| Strept.faecalis 1501 | 0.8 | 0.8 | 0.8 | 1.6 | 1.6 | 1.6 | 0.8 | 1.6 | 3.1 |
| *Staph.aureus MS 353AO | >100 | >100 | >100 | >100 | >100 | 100 | 25 | >100 | >100 |
| *Staph. aureus 0116 | 6.3 | 12.5 | 50 | 50 | 12.5 | 12.5 | 50 | >100 | >100 |
| *Staph.aureus 0119 | 100 | >100 | 100 | >100 | 100 | >100 | >100 | >100 | >100 |
| *Strept.pyogenes 1022 | 0.4 | 0.4 | 0.8 | 1.6 | 0.4 | 0.8 | 6.3 | >100 | >100 |

*Erythromycin, oleandomycin, 16-membered macrolide resistant strains of clinical isolates (macrolide resistant A-group strains) inoculum size 10$^6$/ml, broth dilution method.
**LM = leucomycin The following examples illustrate the present invention:

Rf values in the examples are measured, if not specified, by the following thin layer chromatography:
Carrier: silica gel 60 (Art. 5721, Merck Co.)
Developer:
A: n-hexane:benzene:acetone:ethyl acetate:methanol (90:80:25:60:30)
B. benzene:acetone (3:1)
C: benzene:acetone (5:1)

EXAMPLE 1

3,3″-diacetylleucomycin $A_5$:

To 9-dichloroacetyl leucomycin $A_5$ ($Rf_A=0.55$, $Rf_B=0.11$) (10 g) dissolved in dry acetone (250 ml) was added dry pyridine (11.5 ml), and acetyl chloride was added (9.5 ml) and reacted at 50° C. for 18 hours. The reaction mixture was poured into ice-water (250 ml), adjusted to pH 9.5 by adding aqueous ammonia and extractkd twice with chloroform (250 ml). The chloroform layer was dehydrated by anhydrous sodium sulfate and dried in vacuo to obtain a brownish colored powder.

To the reaction mixture was added water (10 ml), and the mixture was adjusted to pH 2 by adding 1 N-HCl. After separating the aqueous layer, the dichloromethane layer was washed with water and saturated sodium bicarbonate in this order. After drying with anhydrous sodium sulfate, the solution was dried in vacuo to obtain 2′-acetyl-9-dichloroacetyl leucomycin $A_3$.

This was dissolved in dry acetone (10 ml) and thereto was added dry pyridine (2 ml). After adding acetyl chloride (1.4 ml) under cooling with stirring, stirring was continued for 20 hours at 50° C. The reaction mixture was added to ice-water (100 ml) and adjusted to pH 9.5 by adding concentrated aqueous ammonia to obtain a precipitate by filtration, which was washed with water and dried completely. The dried material was chromatographed on a silica gel column by developing with benzene:acetone (18:1). Fractions containing the main component were dried in vacuo to obtain 2′,3″-diacetyl-9-dichloroacetyl leucomycin $A_3$ ($Rf_B=0.62$, $Rf_C=0.36$) (460 mg).

After dissolving the said product in ammonia-saturated methanol solution (10 ml) and allowing it to stand for two hours, solvent was distilled off under reduced pressure. The residue was dissolved in methanol (20 ml) and refluxed with heating for 17 hours. The reaction mixture was dried in vacuo and the residue was treated with silica gel column chromatography by eluting with benzene:acetone (6:1). Eluted fractions showing $Rf_A=0.62$ were collected and dried in vacuo to obtain the product. Yield: 310 mg.

$Rf_A=0.62$, $Rf_B=0.17$

Mass (m/e): 869 (M+), 810 (M+ −59), 768 (M+ −101).

The above 2'-acetyl laucomycin $A_3$ was prepared by the process described in Japanese Patent Publ. No. 53-7434.

EXAMPLE 3

9,3''-diacetyl leucomycin $A_5$:

To leucomycin $A_5$ ($Rf_A=0.38$, $Rf_B=0.04$, $Rf_C=0.01$) (20 g) dissolved in acetic anhydride (40 ml) was added sodium hydrogen sulfate (17.4 g), and the mixture was stirred at room temperature for one hour and at 60° C. for five hours. The reaction mixture was added to ice-water (400 ml) and adjusted to pH 9.5 by adding aqueous ammonia. The precipitate was filtered, washed with water and dried to obtain a powder (22.4 g). This was treated with silica gel column chromatography by eluting with benzene:acetone (9:1). The eluted fractions showing $Rf_A=0.76$ were collected and dried in vacuo to obtain 9,18,2'-triacetyl-3,18-0-cyclo-leucomycin $A_5$ (15.8 g).

$Rf_A=0.76$, $Rf_B=0.50$, $Rf_C=0.22$

Mass (m/e): 897 (M+), 810 (M+ −87), 750 (M+ −87, −60)

NMR (CDCl$_3$, 100 MHz): 2.06 (2'—OAc), 2.10 (18-OAc), 2.20 (9—OAc) ppm.

m.p.: 106°–111° C. (no clear melting point)

UV: $\lambda_{max}^{EtOH}=235.2$ mμ ($\epsilon=2.6\times10^4$)

To the above product (5 g) dissolved in dry ethyl acetate (50 ml) was added dry pyridine (5 ml) and there was added dropwise acetylchloride (4.0 ml) with stirring under ice-cooling. After 10 minutes, the mixture was further reacted at 60° C. for 45 hours. The reaction mixture was added to ice-water (500 ml), adjusted to pH 9.5 by adding aqueous ammonia and extracted twice with chloroform (300 ml). The chloroform layer was washed with water, dried with anhydrous sodium sulfate and dried in vacuo to obtain a powder containing 9,18,2'3''-tetraacetyl-3,18-0-cyclo-leucomycin $A_5$ ($Rf_B=0.71$, $Rf_C=0.46$) (5.06 g).

To this powder dissolved in ethanol (150 ml) was added 5% aqueous sodium carbonate (11.5 ml) and the mixture was stirred at room temperature for 48 hours. Ethanol was distillec off under reduced pressure and the residue was diswolved in chloroform. After washing the solution with water, chloroform was distilled off. The residue was dissolved in methanol (50 ml), refluxed for 18 hours and the reaction mixture was dried in vacuo. The thus-obtained residue was chromatographed on a silica gel column by eluting with benzene:acetone (10:1). Eluted fractions showing $Rf_A=0.67$ were dried in vacuo to obtain the product.

Yield: 1.26 g.

$Rf_A=0.67$, $Rf_B=0.28$

Mass (m/e): 855 (M+), 796 (M+ −59), 768 (M+ −87).

NMR (CDCl$_3$, 100 MHz): 1.43 (3''—CH$_3$), 2.03 (3''—OAc), 2.03 (9—OAc), 9.91 (CHO) ppm.

EXAMPLE 4

3''-acetyl leucomycin $A_3$:

In Example 3, leucomycin $A_5$ was replaced by 9-dichloroacetyl leucomycin $A_5$ to obtain 18,2'-diacetyl-9-dichloroacetyl-3,18-0-cyclo-leucomycin $A_5$ (14.7 g).

$Rf_A=0.79$, $Rf_B=0.51$, $Rf_C=0.22$

NMR (CDCl$_3$, 100 MHz: 2.06 (2'—OAc), 2.11 (18—OAc), 6.38 (9—COCHCl$_2$) ppm.

To the above compound (1 g) dissolvkd in dry ethyl acetate (10 ml) was added γ-collidine (1.5 ml) and there was added dropwise acetyl chloride (0.72 ml) with stirring under ice-cooling. Thereafter, stirring was continued at 60° C. for 20 hours and at 70° C. for 24 hours. The reaction product was dissolved in chloroform (60 ml) and washed with 0.1 N-HCl, water, saturated aqueous sodium bicarbonate and water, in this order. The solution was dried by adding anhydrous magnesium sulfate and concentrated under reduced pressure. The residue was chromatographed on a silica gel (20 g) column by eluting with benzene:acetone (15:1). The eluted fractions showing $Rf_B=0.74$ were dried to obtain 18,2',3''-triacetyl-3,18-0-cyclo-9-dichloroacetyl leucomycin $A_5$ ($Rf_B=0.74$, $Rf_C=0.51$) (604 mg).

The said compound was dissolved in ammonia-saturated methanol (10 ml), allowed to stand for 20 hours and dried in vacuo. The residue was dissolved in methanol (20 ml), refluxed for 15 hours then dried in vacuo. The residue thus obtained was chromatographed on a silica gel (10 g) column by eluting with benzene:acetone (3:1). Fractions showing $Rf_A=0.45$ were concentrated in vacuo to obtain the product (450 mg).

$Rf_A=0.45$, $Rf_B=0.10$

Mass (m/e): 813 (M+), 754 (M+ −59), 726 (M+ −87).

NMR (CDCl$_3$, 100 MHz): 1.43 (3''—CH$_3$), 2.02 (3''—OAc), 9.88 (CHO) ppm.

EXAMPLE 5

3,4''-diacetyl-3''-butyl leucomycin V:

To 2'-acetyl leucomycin $A_5$ (2 g) dissolved in dry dichloromethane (20 ml) was added dry pyridine (0.46 ml) and p-nitrobenzoylchloride (960 mg) and the mixture was allowed to react at room temperature for 15 hours. The reaction mixture was added to water (10 ml), adjusted to pH 2 by adding 1 N HCl, the aqueous layer was separated and the dichloromethane layer was washed with water and saturated aqueous sodium bicarbonate, in this order. After drying the solution with anhydrous sodium sulfate, the residue was dried in vacuo to obtain almost quantitatively 2'-acetyl-9-p-nitrobenzoyl leucomycin $A_5$. To this compound dissolved in dry pyridine (20 ml) was added acetic anhydride (2.5 ml) and thk reaction was continued for three days at 100° C. The reaction mixture was concentrated under reduced pressure and the residue was dissolved in chloroform (20 ml). Water (10 ml) waw added thereto, and the mixture was adjusted to pH 2 by addition of 1 N HCl. The chloroform layer was separated and washed with water and saturated aqueous sodium bicarbonate solution, in this order, then dried by adding anhydrous sodium sulfate and dried in vacuo. To the residue was added ammonia-saturated methanol solution (50 ml), and the mixture was allowed to stand overnight and concentrated in vacuo. The residue was dissolved in methanol (50 ml), refluxed overnight and dried in vacuo. The thus-formed residue was chromatographed on a silica gel column by developing with benzene:acetone (6:1). The eluate showing $Rf_A=0.58$ was concentrated in vacuo to obtain the product. Yield: 225 mg.

$Rf_A=0.58$, $Rf_B=0.17$

Mass (m/e): 855 (M+), 796 (M+ −59), 768 (M+ −87)

The above 2'-acetyl leucomycin A₅ was prepared by the process described in Japanese Patent Publ. No. 53-7434.

EXAMPLE 6

4"-acetyl-3"-isovaleryl leucomycin U:

To 2'-acetyl leucomycin A₃ (2 g) dissolved in dry dichloromethane (20 ml) was added dry pyridine (0.43 ml) and p-nitrobenzoylchloride (896 mg) and the mixture was reacted for three days at room temperature. To the reaction mixture was added water (10 ml), and the mixture was adjusted to pH 2 by adding 1 N HCl, the aqueous layer was separated and the dichloromethane layer was washed with water, saturated aqueous sodium bicarbonate and water, in this order. After drying with sodium sulfate, the solution was entirely dried to obtain 2'-acetyl-9-p-nitrobenzoyl leucomycin A₃. This was dissolved in dry pyridine (20 ml), acetic anhydride (2.5 ml) was added thereto and the mixture was reacted at 100° C. for three days. The reaction mixture was concentrated in vacuo, adding chloroform (20 ml) and water (20 ml), and the aqueous layer was adjusted to pH 2 and separated. The chloroform layer was washed with water and saturated aqueous sodium bicarbonate, and dried in vacuo. The residue was dissolved in ammonia-saturated methanol (50 ml), allowed to stand for three days at room temperature then concentrated in vacuo. The thus-obtained residue was dissolved in methanol (50 ml), refluxed by heating for 20 hours and concentrated in vacuo. The residue was chromatographed on a silica gel column by developing with benzene:acetone (7:1) and the eluted fractions showing $Rf_A=0.60$ were collected and dried in vacuo to obtain the product. Yield: 190 mg.

$Rf_A=0.60$, $Rf_B=9.16$

Mass (m/e): 896 (M+), 810 (M+ −59), 768 (M+ −101)

EXAMPLE 7

9,4"-diacetyl-3"-butylyl leucomycin V:

To 9,18,2'-tetraacetyl-3,18-0-cyclo-leucomycin A₅ (5.0 g), obtained in Example 3, dissolved in dry pyridine (30 ml) was added acetic anhydride (15 ml) and the mixture was reacted at 100° C. for 39 hours. The reaction mixture was added to water (500 ml) containing aqueous ammonia (pH 9.5) and extracted twice with chloroform (300 ml). The extract was washed with water (500 ml), dried by adding anhydrous sodium sulfate and dried in vacuo to obtain a powder containing 9,18,2',4"-tetraacetyl-3"-butylyl-3,18-0-cyclo-leucomycin V as a main component (5.05 g).

$Rf_B=0.73$, $Rf_C=0.50$

Mass (m/e): 939 (M+), 880 (M+ −59), 852 (M+ −87).

To this powder dissolved in ethanol (150 ml) was added 5% aqueous sodium carbonate (11.5 ml), and the mixture was allowed to stand at room temperature for 45 hours, and at 70° C. for 12 hours. Ethanol was distilled off under reduced pressure and the residue was dissolved in chloroform (150 ml), which was washed twice with water (100 ml), dehydrated by adding anhydrous sodium sulfate and dried in vacuo to obtain a powder (4.73 g). The powder was dissolved in methanol (50 ml), refluxed for 17 hours then concentrated in vacuo. The residue was chromatographed on a silica gel column by developing with benzene:acetone (10:1), and the eluted fractions showing Rf_A—0.66 were collected and dried in vacuo to obtain the product. Yield: 2.12 g.

$Rf_A=0.66$, $Rf_B=0.28$

Mass (m/e): 855 (M+), 796 (M+ −59), 768 (M+ −87)

NMR (CDCl₃, 100 MHz): 1.44 (3"—CH₃), 2.02 (9-OAc), 2.15 (4"—OAc), 9.90 (CHO) ppm.

EXAMPLE 8

4"-acetyl-3"-butylyl leucomycin V:

In Example 3, leucomycin A₃ was replaced by 9-chloroacetyl leucomycin A₅ to obtain 18,2'-diacetyl-9-chloroacetyl-3,18-0-cyclo-leucomycin A₅.

Yield: 74%.

$Rf_A=0.78$, $Rf_B=0.50$, $Rf_C=0.22$

NMR (CDCl₃, 100 MHz): 2.07 (3H, 2'—OAc), 2.12 (3H, 18—OAc), 4.31 (2H, 9—COCH₂Cl) ppm.

To the above substance (5 g) dissolved in acetic anhydride (15 ml) was added potassium carbonate (3.5 g), and the mixture was reacted at 90° C. for 26 hours and at 100° C. for 6 hours. The reaction mixture was poured into water (200 ml), adjusted to pH 9.5 by adding aqueous ammonia and extracted twice with chloroform (200 ml). The extract was washed with water, dehydrated with anhydrous sodium sulfate and dried in vacuo to obtain a powder (5.07 g). The powder was chromatographed on a silica gel column by eluting with benzene:acetone (16:1). Eluates showing $Rf_B=0.72$ were collected and concentrated in vacuo to obtain 18,2',4"-triacetyl-3"-butylyl-9-chloroacetyl-3,18-0-cyclo-leucomycin V ($Rf_B=0.72$, $Rf_C=0.47$) (2.47 g), which was dissolved in ammonia-saturated methanol solution (60 ml), allowed to stand at room temperature for 17 hours and dried in vacuo. The residue was dissolved in methanol (60 ml) and refluxed for 20 hours. The reaction mixture was dried in vacuo and chromatographed on a silica gel column by developing with benzene:acetone (4:1). Eluted fractions showing $Rf_A=0.45$ were collected and dried to obtain the product. Yield: 1.72 g.

$Rf_A=0.45$, $Rf_B=0.10$

Mass (m/e): 813 (M+), 754 (M+ −59), 726 (M+ −87)

NMR (CDCl₃, 100 MHz): 1.44 (3"—CH₃), 2.16 (4"—OAc), 9.93 (CHO) ppm.

EXAMPLE 9

3"-acetyl-SF-837:

To SF-837 substance (4.0 g) dissolved in acetone (40 ml) was added acetic anhydride (2.5 ml) and the mixture was stirred for three hours at room temperature. The reaction mixture was added ice-water (400 ml), the pH was adjusted to 8.5 by adding 7% aqueous ammonia and the mixture was extracted twice with benzene (200 ml). The benzene layer was dehydrated with anhydrous magnesium sulfate and dried in vacuo to obtain 2'-acetyl-SF-837 substance ($Rf_A=0.66$, $Rf_B=0.33$) (4.15 g, yield: 98.6%).

To this substance dissolved in acetone (40 ml) was added dry pyridine (1.34 ml) and dichloroacetyl chloride (1.07 ml) was added dropwise under cooling, then the mixture was stirred for one hour and 20 minutes under cooling. The reaction mixture was added to ice-water (400 ml) and adjusted to pH 9.5 with 7% aqueous ammonia. The precipitate was filtered, washed and dried completely in vacuo to obtain a powder of 2'-acetyl-9-dichloroacetyl-SF-837 substance ($Rf_A=0.83$, $Rf_B=0.71$, $Rf_C=0.45$) (4.13 g).

To 2'-acetyl-9-dichloroacetyl-SF-837 substance (1 g) dissolved in dry ethyl acetate (10 ml) was added γ-collidine (1.5 ml) and acetyl chloride (0.73 ml) was added dropwise under ice-cooling. Stirring was continued for two hours at room temperature followed by stirring at 70° C. for 48 hours. The reaction mixture was poured into ice-water (50 ml), adjusted to pH 5.7 by adding 7% aqueous ammonia and extracted twice with chlorofom (50 ml).

The extract was dehydrated with anhydrous magnesium sulfate and concentrated in vacuo. Residue was dissolved in acetone (10 ml), added to ice-water (100 ml) and the mixture was adjusted to pH 9.5 by adding aqueous ammonia. The precipitate was filtered, washed with water and dried to obtain the product (850 mg). This was chromatographed on a silica gel column by developing with benzene:acetone (20:1). The eluate showing $Rf_C=0.71$ was concentrated in vacuo to obtain 2′,3″-diacetyl-9-dichloroacetyl-SF-837 substance ($Rf_B=0.87$, $Rf_C=0.71$) (550 mg).

The compound was dissolved in ammonia-saturated methanol solution (10 ml), allowed to stand for two hours at room temperature, dried in vacuo, dissolved in methanol (20 ml) and heated at 70° C. overnight. The reaction mixture was dried in vacuo and the residue was chromatographed on a silica gel column by eluting with benzene:acetone (5:1). The eluate showing $Rf_A=0.58$ was concentrated in vacuo to obtain the product (420 mg).

$Rf_A=0.58$, $Rf_B=0.22$

Mass (m/e): 855 (M+), 796 (M+−59), 782 (M+−73)

NMR (CDCl₃, 100 MHz): 1.43 (3″—CH₃), 2.01 (3″-Ac), 2.57 [3′-N(CH₃)₂], 3.58 (4—)CH₃), 9.72 (CHO) ppm.

EXAMPLE 10

3-acetyl-3″-propionyl leucomycin A₅:

In Example 2, 2′-acetyl leucomycin A₃ was replaced by 2′-acetyl leucomycin A₅ to prepare 2′-acetyl-9-dichloroacetyl leucomycin A₅.

To 2′-acetyl-9-dichloroacetyl leucomycin A₅ (2 g) dissolved in dry acetone (10 ml) was added dry pyridine (1.6 ml). There was further added acetyl chloride (1.3 ml) under ice-cooling, and the mixture was reacted for 2.5 hours at 45° C. The reaction mixture was added to ice-water (100 ml), adjusted to pH 9.5 by adding aqueous ammonia and extracted twice with chloroform (50 ml). The chloroform layer was dehydrated with anhydrous sodium sulfate and dried to obtain 3,2″-diacetyl-9-dichloroacetyl leucomycin A₅ (2.02 g).

$Rf_A=0.84$, $Rf_B=0.67$, $Rf_C=0.36$

To the 3,2″-diacetyl-9-dichloroacetyl leucomycin A₅ (1.5 g) dissolved in dry dioxane (15 ml) was added γ-collidine (2.26 ml) and propionyl chloride (1.39 ml) under cooling and the mixture was reacted at 100° C. for 44 hours. The reaction mixture was added to ice-water (150 ml) and extracted with benzene (150 ml). The benzene layer was washed with diluted aqueous ammonia and concentrated in vacuo. The residue was dissolved in a small amount of benzene and chromatographed on a silica gel column by eluting with benzene:acetone (25:1). The eluate showing $Rf_C=0.74$ was dried to obtain 3,2″-diacetyl-9-dichloroacetyl-3″-propionyl leucomycin A₅ (562 mg).

$Rf_B=0.83$, $Rf_C=0.74$

NMR (CDCl₃, 100 MHz): 1.43 (3″—CH₃), 2.03 (2′-Ac), 2.29 (3-Ac), 2.46 [3′-N(CH₃)₂], 3.52 (4—OCH₃), 6.04 (9-COCHCl₂), 9.76 (CHO) ppm.

The product hereinabove was dissolved in ammonia-saturated methanol solution (10 ml) and allowed to stand for one hour. The reaction mixture was concentrated in vacuo and the residue was dissolved in methanol (20 ml), refluxed foa 16 hours, then dried in vacuo. The residue was dissolved in a small amount of benzene and chromatographed on a silica gel column by eluting with benzene:acetone (10:1). Fractions showing $Rf_A=0.57$ were dried in vacuo to obtain the product (420 mg).

$Rf_A=0.57$, $Rf_B=0.19$

Mass (m/e): 869 (M+), 796 (M+−73), 782 (M+−87)

NMR (CDCl₃, 100 MHz): 1.44 (3″—CH₃), 2.30 (3-Ac), 2.60 [3′-N(CH₃)₂], 3.59 (4—OCH₃), 9.75 (CHO) ppm.

EXAMPLE 11

3-acetyl-3″-propionyl leucomycin A₅:

In Example 10, 2′-acetyl-9-dichloroacetyl leucomycin A₅ was replaced by 2′-acetyl-9-chloroacetyl leucomycin A₅ to obtain tbe product (400 mg).

The above 2′-acetyl-9-chloroacetyl leucomycin A₅ was prepared by acetylation of 9-chloroacetyl leucomycin obtained by the process described in Japanese Patent Open. No. 50-96584, at the 2′ position (2′-acetylation) described in Japanese Patent Publ. No. 53-7434.

EXAMPLE 12

9-acetyl-3″-propionyl leucomycin A₅:

9,18,2′-triacetyl-3,18-0-cyclo-leucomycin A₅ (10 g) obtained by the process in Example 3 was dissolved in ethyl acetate (100 ml), then there was added γ-collidine (16 ml) and propionylchloride (9.69 ml) under cooling and the mixture was stirred at 70° C. for four days. Chloroform (200 ml) was added to the reaction mixture, which was washed twice with water (200 ml) and once with diluted aqueous ammonia (200 ml). The chloroform layer was dehydrated by adding anhydrous sodium sulfate and dried in vacuo. Thk residue was dissolved in a small amount of benzene and chromatographed on a silica gel column by eluting with benzene:acetone (17:1). Fractions showing $Rf_B=0.75$ were dried in vacuo to obtain 9,18,2′-triacetyl-3,18-0-cyclo-3″-propionyl leucomycin A₅ ($Rf_B=0.75$, $Rf_C=0.56$) (4.02 g).

The said substance was dissolved in ammonia-saturated methanol solution (40 ml), allowed to stand for 17 hours and dried in vacuo. The residue was dissolved in methanol (50 ml), refluxed for 17 hours, then dried in vacuo.

The residue was chromatographed on a silica gel column by eluting with benzene:acetone (7:1). Fractions showing $Rf_A=0.67$ were collected and dried in vacuo to obtain the product (3.1 g).

$Rf_A=0.67$, $Rf_B=0.33$, $Rf_C=0.13$

Mass (m/e): 869 (M+), 796 (M+−73), 783 (M+−87)

NMR (CDCl₃, 100 MHz): 1.42 (3″—CH₃), 2.00 (9-Ac), 2.54 [3′—N(CH₃)₂], 3.53 (4—OCH₃), 9.84 (CHO) ppm.

EXAMPLE 13

3″-propionyl leucomycin A₅:

18,2′-diacetyl-9-dichloroacetyl-3,18-0-cyclo-leucomycin A₅ (5 g) obtained in Example 4 was dissolved in dry dioxane (50 ml), to which there was added dry γ-collidine (7.5 ml), and propionyl chloride (4.5 ml) was added dropwise under ice-cooling and the mixture was stirred at 90° C. for 20 hours. Benzene (500 ml) was added thereto, and the mixture was washed twice with water (50 ml) and once with diluted aqueous ammonia (500 ml). The benzene layer was dehydrated by adding anhydrous sodium sulfate and dried in vacuo to obtain a powder (5.1 g). This powder was chromatographed on a silica gel column by eluting with benzene:acetone (18:1). Fractions showing $Rf_B=0.78$ were dried to obtain 18,2'-diacetyl-9-dichloroacetyl-3,18-0-cyclo-3"-propionyl leucomycin $A_3$ (2.8 g).

Recrystallization was effected with benzene-n-hexane to yield colorless crystals, m.p. 177°–179° C.

The crystals hereinabove were dissolved in ammonia-saturated methanol solution (50 ml), allowed to stand for four hours at room temperature and dried in vacuo.

The residue was dissolved in methanol (50 ml), refluxed for 16 hours then dried in vacuo. The residue was dissolved in a small amount of benzene and chromatographed on a silica gel column by eluting with benzene:acetone (6:1). Fractions showing $Rf_A=0.47$ were dried to obtain the product (2.1 g).

$Rf_A=0.47$, $Rf_B=0.14$

Mass (m/e): 827 (M+), 754 (M+ −73), 740 (M+ −87)

NMR (CDCl$_3$, 100 MHzO: 1.44 (3"—CH$_3$), 2.57 [3'—N(CH$_3$)$_2$], 3.56 (4—OCH$_3$), 9.86 (CHO) ppm.

EXAMPLE 14

3"-butylyl leucomycin $A_5$:

To 18,2'-diacetyl-3,18-0-cyclo-9-dichloroacetyl leucomycin $A_5$ (5 g) obtained in Example 4 dissolved in dry dioxane (50 ml) was added dry γ-collidine (7.51 ml), butylyl chloride (5.37 ml) was added under ice-cooling and the mixture was stirred at 90° C. for 16 hours. Benzene (500 ml) was added to the reaction mixture, which was washed twice with water and once with dilute aqueous ammonia (500 ml). The benzene layer was dehyarated by adding anhydrous sodium sulfate and dried. The residue was chromatographed on a silica gel column by eluting with benzene:acetone (20:1). Fractions showing $Rf_C=0.65$ were dried in vacuo to obtain 18,2'-diacetyl-3,18-0-cyclo-9-dichloroacetyl-3"-butyl leucomycin $A_5$ (2.72 g).

$Rf_B=0.80$, $Rf_C=0.65$

NMR (CDCl$_3$, 100 MHz): 1.43 (3"—CH$_3$), 2.06 (2'-Ac), 2.11 (18-Ac), 2.48 [3'—N(CH$_3$)$_2$], 3.46 (4—OCH$_3$), 6.36 (9—COCHCl$_2$)

m.p.: 196°–198° C. (recrystallized colorless crystals from benzene-n-hexane)

The above product was dissolved in ammonia-saturated methanol solution (20 ml), allowed to stand for 16 hours and dried in vacuo. The residue was dissolved in methanol (50 ml), refluxed for 16 hours then dried. The residue was chromatographed on a silica gel column by eluting with benzen:acetone (6:1). Fractions showing $Rf_A=0.48$ were dried to obtain the product (1.7 g).

$Rf_A=0.48$, $Rf_B=0.15$

Mass (m/e): 841 (M+), 754 (M+ −87).

NMR (CDCl$_3$, 100 MHZ): 1.42 (3"—CH$_3$), 2.57 [3'—N(CH$_3$)$_2$], 3.55 (4—OCH$_3$), 984 (CHO) ppm.

EXAMPLE 15

4"-acetyl-3,3"-dipropionyl leucomycin V:

2'-acetyl-SF-837 substance (1 g) obtained in Example 9 was dissolved in dry dichloromethane (10 ml), dry pyridine (0.23 ml) and p-nitrobenzoyl chloride (480 ml) were added, and then the mixture was stirred at room temperature for 17 hours. To the reaction mixture was added an equal amount of water, and the mixture was stirred well and the dichloromethane layer was separated and washed with water (10 ml) and saturated aqueous sodium bicarbonate (10 ml). After dehydrating with anhydrous sodium sulfate, the solution was dried to obtain 2'-acetyl-9-p-nitrobenzoyl-SF-837 substance ($Rf_B=0.72$, $Rf_C=0.44$). This substance was dissolved in dry pyridine, acetic anhydride (1.2 ml) was added therein, and the mixture was reacted at 90° C. for three days. The reaction mixture was concentrated in vacuo and dissolved in chloroform (10 ml) and was washed witb diluted hydrochloric acid (10 ml), water (10 ml) and saturated aqueous sodium bicarbonate (10 ml), in this order. The residue was dissolved in a small amount of benzene and chromatographed on a silica gel column by eluting with benzene:acetone (20:1). The main eluate was concentrated in vacuo and dissolved in ammonia-saturated methanol (15 ml), allowed to stand at room temperature for two days, and dried in vacuo, then methanol (20 ml) was added and the mixture was refluxed for 18 hours. The reaction mixture was dried in vacuo and chromatographed on a silica gel column by eluting with benzene:acetone (7:1). The eluate showing $Rf_A=0.56$ was dried to obtain the product (280 mg).

$Rf_A=0.56$, $Rf_B=0.18$

Mass (m/e): 855 (M+), 796 (M+ −59), 782 (M+ −73).

EXAMPLE 16

3"-butylyl-4"-propionyl leucomycin V:

18,2-diacetyl-9-dichloroacetyl-3,18-0-cyclo-leucomycin $A_5$ (5 g) obtained in Example 4 was dissolved in dry pyridine (30 ml) to which was added propionic anhydride (15 ml) and the mixture was reacted at 100° C. for 40 hours. The reaction mixture was poured into ice-water (500 ml), adjusted to pH 9.5 by adding aqueous ammonia and extracted twice with chloroform (300 ml). The chloroform layer was washed with water, dehydrated by adding anhydrous sodium sulfate then dried in vacuo to obtain a powder (5.13 g). This powder was chromatographed on a silica gel column by eluting with benzene:acetone (18:1). The eluate showing $Rf_C=0.63$ was dried to obtain 18,2'-diacetyl-3"-butylyl-3,18-0-cyclo-9-dichloroacetyl-4"-propionyl leucomycin V (1.5 g).

This substance was dissolved in ammonia-saturated methanol solution (30 ml), allowed to stand for 16 hours and dried in vacuo. The residue was dissolved in methanol (50 ml), refluxed for 20 hours, then dried in vacuo. The thus-formed residue was chromatographed on a silica gel column by eluting with benzene:acetone (6:1). The eluate showing $Rf_A=0.46$ was dried in vacuo to obtain the product (1.2 g).

$Rf_A=0.46$, $Rf_B=0.11$

Mass (m/e): 827 (M+), 754 (M+ −73), 740 (M+ −87).

NMR (CDCl$_3$, 190 MHz): 1.43 (3"—CH$_3$), 2.57 [3'—N(CH$_3$)$_2$], 3.54 (4—OCH$_3$), 9.87 (CHO) ppm.

EXAMPLE 17

3"-isovaleryl leucomycin $A_5$:

To 2'-acetyl leucomycin $A_5$ (5 g) dissolved in dry dichloromethane (25 ml) was added dry pyridine (1.64 ml). Dichloroacetyl chloride (1.77 ml) was added dropwise under ice-cooling and the mixture was stirred for one hour. Cold water was added to the reaction mixture, which was extracted with dichloromethane (25 ml). After drying the dichloromethane layer with anhydrous magnesium sulfate, it was dried in vacuo to obtain quantitatively 2'-acetyl-3,9-dichloroacetyl leucomycin $A_5$.

To the above product (5 g) dissolved in dry dioxane (50 ml) was added γ-collidine (7.87 ml). Isovaleryl chloride (6.62 ml) was added dropwise under cooling, then the mixture was stirred at 90° C. for 80 hours. The reaction mixture was poured into cold water (500 ml) and extracted twice with benzene (400 ml). The benzene layer was dehydrated by adding anhydrous magnesium sulfate and dried in vacuo. The residue was dissolved in methanol (20 ml), ammonia-saturated methanol solution (20 ml) was added thereto and the mixture was stirred at room temperature for 30 minutes. The reaction mixture was poured into cold water (500 ml), extracted twice with benzene (400 ml), dehydrated with anhydrous magnesium sulfate and dried in vacuo. The residue was chromatographed on a silica gel column by gradient elution with benzene:acetone (15:1, 7:1 and 5:1). The main fractions were collected and dried in vacuo to obtain crude 2'-acetyl-3"-isovaleryl leucomycin $A_5$ (1.25 g). This was dissolved in methanol (20 ml), refluxed by heating for 20 hours and dried in vacuo. The residue was again chromatographed on a silica gel column by eluting with benzene:acetone (9:1). Fractions showing $Rf_A = 0.48$ were dried to obtain the product (830 mg).

$Rf_A = 0.48$

Mass (m/e): 855 (M+), 768 (M+ −87), 754 (M+ −101).

NMR (CDCl$_3$, 100 MHz): 1.42 (3"—CH$_3$), 9.89 (CHO) ppm.

EXAMPLE 18

3"-acetyl leucomycin $A_1$:

To 2'-acetyl leucomycin $A_1$ (5 g) dissolved in dry dichloromethane (25 ml) was added dry pyridine (1.64 ml). Dichloroacetyl chloride (1.77 ml) was added dropwise under ice-cooling and the mixture was stirred for one hour. To the reaction mixture was added cold water (25 ml) and the mixture was extracted with dichloromethane (25 ml). The dichloromethane layer was dehydrated with anhydrous magnesium sulfate and dried in vacuo to obtain a quantitative amount of 2'-acetyl-3,9-dichloroacetyl leucomycin $A_1$.

To the above product (5 g) dissolved in dry ethyl acetate (50 ml) was added γ-collidine (9.4 ml) under ice-cooling and acetyl chloride (4.6 ml) and the mixture was stirred for 72 hours at 70° C.

The reaction mixture was poured into cold water (250 ml) and extracted twice with chloroform (150 ml). The chloroform layer was washed with dilute hydrochloric acid (pH 2), water and saturated aqueous sodium bicarbonate, in this order, dehydrated with anhydrous sodium sulfate and dried in vacuo. The residue was dissolved in methanol (10 ml). Ammonia-saturated methanol solution (10 ml) was added and the mixture was stirred at room temperature for 30 minutes. The reaction mixture was poured into cold water (250 ml) and extracted twice with chloroform. The chloroform layer was dehydrated with anhydrous magnesium sulfate and dried in vacuo. The residue was chromatographed on a silica gel column by diluting with benzene:acetone (8:1) and the eluate was concentrated to obtain a crude powder (1.4 g) of 2',3"-diacetyl leucomycin $A_1$. This crude powder was dissolved in methanol (20 ml), refluxed for 20 hours and dried in vacuo. The residue was again chromatographed on a silica gel column by eluting with benzene:acetone (6:1). The eluate showing $Rf_A = 0.46$ was dried in vacuo to obtain the product (716 mg).

$Rf_A = 0.46$

Mass (m/e): 827 (M+), 768 (M+ −59), 726 (M+ −101).

NMR (CDCl$_3$, 100 MHz): 1.43 (3"—CH$_3$), 2.00 (3"—OAc), 9.89 (CHO) ppm.

EXAMPLE 19

3"-acetyl leucomycin $A_5$:

To 2'-acetyl leucomycin $A_5$ (65 g) dissolved in dry dichloromethane (300 ml) was added dry pyridine (44 ml) and trimethylchlorosilane (39 ml), then the mixturk was stirred for one houa at room temperature. The reaction mixture was poured into water (2 l) and extracted with chlorofom (500 ml). The extract was washed with 0.1 N HCl, water and 3% aqueous ammonia, in this order, dehydrated with anhydrous magnesium sulfate and dried in vacuo to obtain crude 2'-acetyl-3,9-di(trimethylsilyl)leucomycin $A_5$ (69 g).

The above substance was dissolved in dry ethyl acetate (200 ml), tribenzylamine (227 g) was added thereto, and there was further added acetyl chloride (51 ml) under ice-cooling, then the mixture was stirred at 70° C. for 40 hours. The reaction mixture was poured into water (2 l), adjusted to pH 9.5 by adding aqueous ammonia, and extracted with chloroform (1 l.) The extract was washed with water, dehydrated by adding anhydrous magnesium sulfate and concentrated in vacuo to obtain 2',3"-diacetyl-3,9-di(trimethylsilyl)leucomycin $A_5$, in which a small amount of 18,2',3"-triacetyl-3,9-di(trimethylsilyl)-17-dehydro leucomycin $A_5$ and a large amount of tribenzylamine were contained. Thereto was added ammonia-saturated methanol solution (250 ml) under ice-cooling and the mixture was stirred for 1.5 hours at room temperature. The reaction was poured into water (2 l.) and extracted with chloroform (1 l.) The extract was washed with water, dehydrated with anhydrous magnesium sulfate and dried in vacuo. The residue was dissolved in cold methanol (600 ml) and the insoluble tribenzylamine was filtered off. The filtrate was refluxed by heating for 20 hours then dried in vacuo to obtain crude 3"-acetyl-3,9-di(trimethylsilyl)-leucomycin $A_5$ (69 g).

The substance was dissolved in acetic acid:tetrahydrofuran:water (3:1:1) (250 ml) and stirred for one hour at room temperature. To the reaction mixture was added chloroform (1 l.) and the mixture was washed with 3% aqueous ammonia. The chloroform layer was dehydrated with anhydrous magnesium sulfate and dried in vacuo to obtain crude 3"-acetyl leucomycin $A_5$ (64 g), which was dissolved in a small amount of benzene and charged on a column of silica gel. Elution was gradually carried out with benzene:acetone (10:1, 8:1, 6:1). Each fraction was checked by silica gel thin layer chromatography and the fractions showing $Rf_A = 0.45$ were collected and dried in vacuo to obtain the purified product (45.5 g, yield: 70%).

$Rf_A = 0.45$, $Rf_B = 0.10$

Mass (m/e): 813 (M+), 754 (M+ −59), 726 (M+ −87)

Potency: 2850 γ/mg (as compared with standard leucomycin).

EXAMPLE 29

3"-propionyl leucomycin $A_5$:

To 2'-acetyl leucomycin $A_5$ (65 g) dissolved in dry dichloromethane (300 ml) was added dry pyridine (44 ml) and trimethylchlorosilane (39 ml) and was stirred for one hour at room temperature. The reaction mixture was poured into water (2 l.) and extracted with chloroform (500 ml). The extract was washed with 0.1 N HCl, water and 3% aqueous ammonia, in this order, dehydrated with anhydrous magnesium sulfate and dried in vacuo to obtain crude 2'-acetyl-3,9-di(trimethylsilyl)-leucomycin A₅ (70 g).

To the above crude substance dissolved in dry dioxane (200 ml) was added tribenzylamine (230 g). Propionyl chloride (65 ml) was added under ice-cooling and the mixture was stirred at 90° C. for 24 hours. The reaction mixture was poured into water (2 l.), adjusted to pH 9.5 by adding aqueous ammonia and extracted with chloroform (1 l.). The extract was dehydrated with anhydrous magnesium sulfate and dried to obtain 2'-acetyl-3,9-di(trimethylsilyl)-3''-propionyl leucomycin A₅, containing a small amount of 2'-acetyl-3,9-di(-trimethylsilyl)-18,3'-dipropionyl-17-dehydro leucomycin A₅ and a large amount of tribenzylamine. Thereto was added ammonia-saturated methanol solution (250 ml) and the mixture was stirred at room temperature for 1.5 hours. The reaction mixture was poured into water (2 l.) and extracted with chloroform (1 l.). The extract was washed with water, dehydrated with anhydrous magnesium sulfate and dried in vacuo. The residue was dissolved in cold methanol and the insoluble tribenzylamine was filtered off. The filtrate was refluxed for 20 hours and dried in vacuo to obtain crude 3,9-di(trimethylsilyl)-3''-propionyl leucomycin A₅. This substance was dissolved in acetic acid:tetrahydrofuran:water (3:1:1) (250 ml) and stirred for one hour at room temperature. To the reaction mixture was added chloroform (1 l.) and the mixture was washed with 3% aqueous ammonia. The chloroform layer was dehydrated with anhydrous magnesium sulfate and dried in vacuo to obtain crude 3''-propionyl leucomycin A₅ (60 g), which was dissolved in a small amount of benzene and charged on a silica gel column. Elution was carried by mixtures of benzene:acetone (15:1, 10:1, 8:1). Each fraction was checked by silica gel thin layer chromatorgraphy and the fractions showing $Rf_A=0.57$ were collected and dried in vacuo to obtain the purified product (52.5 g, yield: 79.4%).

$Rf_A=0.57$, $Rf_B=0.14$

Mass (m/e): 827 (M⁺), 754 (M⁺−73), 740 (M⁺−87)

Potency: 2850 γ/mg (as compared with standard leucomycin).

EXAMPLE 21

3''-acetyl leucomycin A₄ (3,3''-diacetyl leucomycin A₅):

To 2'-acetyl leucomycin A₅ (30 g) dissolved in dry dichloromethane (150 ml) was added dry pyridine (6 ml) under ice-cooling and trimethylchlorosilane (5.69 ml) and stirred for one hour at room temperature. The reaction mixture was washed with 0.1 N HCl, water and 3% aqueous ammonia, in this order, dehydrated with anhydrous magnesium sulfate and dried in vacuo to obtain crude 2'-acetyl-9-trimethylsilyl leucomycin A₅ (30.2 g).

The above crude material was dissolved in dry dioxane (50 ml), tribenzylamine (113 g) and acetyl chloride (25 ml) were added therein and the mixture was stirred for 40 hours at 80° C. The reaction mixture was poured into water (1 l.), adjusted to pH 9.5 with aqueous ammonia and extracted with chloroform (500 ml). The extract was dehydrated with anhydrous magnesium sulfate and concentrated in vacuo. To the residue was added ammonia-saturated methanol solution (50 ml) and the mixture was stirred for two hours at room temperature. The reaction mixture was poured into water (1.5 l.) and extracted with chloroform (500 ml). The chloroform layer was dehydrated with anhydrous magnesium sulfate and dried in vacuo. The residue was dissolved in cold methanol (200 ml), and the insoluble tribenzylamine was filtered off. The filtrate was refluxed for 20 hours and dried to obtain crude 3,3''-diacetyl-9-trimethylsilyl leucomycin A₅.

This crude material was dissolved in acetic acid:tetrahydrofuran:water (3:1:1) (125 ml) and stirred for two hours at room temperature. To the reaction mixture was added chloroform (500 ml) and the mixture was washed with 3% aqueous ammonia. The chloroform layer was dehydrated with anhydrous magnesium sulfate and dried in vacuo to obtain crude 3,3''-diacetyl leucomycin A₅ (29.8 g). This substance was dissolved in a small amount of benzene, charged on a column of silica gel and gradiently eluted with benzene:acetone (10:1, 8:1, 6:1). Fractions were checked by silica gel thin layer chromatography, and the fractions showing $Rf_A=0.58$ were collected and dried in vacuo to obtain the purified product (21.2 g, yield: 67.2%).

$Rf_A=0.58$, $Rf_B=0.15$

Mass (m/e): 855 (M⁺), 796 (M⁺−59), 768 (M⁺−87).

What is claimed is:

1. A compound of the formula

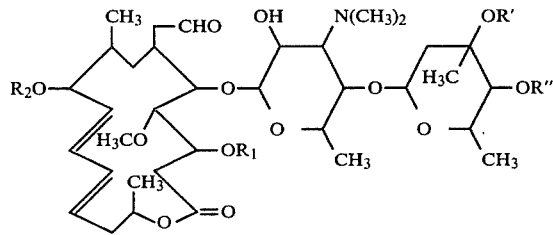

wherein R₁ is hydrogen or C₂₋₃ alkanoyl, R₂ is hydrogen or C₂₋₄ alkanoyl, at least one of R₁ and R₂ being hydrogen, and one of R' and R'' is R₃ and the other is R₄, in which R₃ is C₂₋₆ alkanoyl and R₄ is C₂₋₅ alkanoyl, or a pharmaceutically acceptable salt thereof.

2. A compound as claimed in claim 1, of the formula

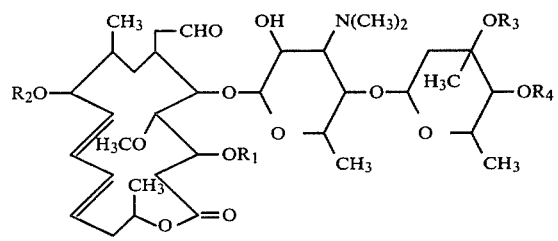

wherein R₁ is hydrogen or C₂₋₃ alkanoyl, R₂ is hydrogen or C₂₋₄ alkanoyl, at least one of R₁ and R₂ being hydrogen, R₃ is C₂₋₆ alkanoyl and R₄ is C₂₋₅ alkanoyl, or a pharmaceutically acceptable salt thereof.

3. A compound as claimed in claim 2, wherein R₁ is C₂₋₃ alkanoyl, R₂ is hydrogen, and R₃ and R₄ have the same meanings hereinabove, or a pharmaceutically acceptable salt thereof.

4. A compound as claimed in claim 3, wherein R₄ is propionyl, butylyl or isovaleryl, and R₁, R₂ and R₃ have the same meanings hereinabove, or a pharmaceutically acceptable salt thereof.

5. A compound as claimed in claim 2, wherein $R_1$ is hydrogen and $R_2$ is $C_{2-4}$ alkanoyl, and $R_3$ and $R_4$ have the same meanings as in claim 2, or a pharmaceutically acceptable salt thereof.

6. A compound as claimed in claim 5, wherein $R_4$ is butylyl or isovaleryl, $R_1$ is $C_{2-3}$ alkanoyl, $R_2$ is hydrogen and $R_3$ is $C_{2-6}$ alkanoyl, or a pharmaceutically acceptable salt thereof.

7. A compound as claimed in claim 2, wherein $R_1$ or $R_2$ is hydrogen and $R_3$ and $R_4$ have the same meanings as in claim 2, or a pharmaceutically acceptable salt thereof.

8. A compound as claimed in claim 7, wherein $R_4$ is butylyl or isovaleryl, and $R_1$, $R_2$ and $R_3$ have the same meanings as in claim 7, or a pharmaceutically acceptable salt thereof.

9. A compound as claimed in claim 1, of the formula

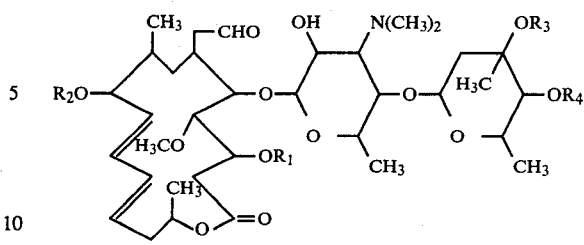

wherein $R_1$ is hydrogen or $C_{2-3}$ alkanoyl, $R_2$ is hydrogen or $C_{2-4}$ alkanoyl, at least one of $R_1$ and $R_2$ being hydrogen, $R_3$ is $C_{2-6}$ alkanoyl, and $R_4$ is $C_{2-5}$ alkanoyl, or a pharmaceutically acceptable salt thereof.

10. A compound as claimed in claim 9, wherein $R_1$ is $C_{2-3}$ alkanoyl, and $R_2$ is hydrogen or a pharmaceutically acceptable salt thereof.

11. A compound as claimed in claim 10, wherein $R_4$ is propionyl, butylyl or isovaleryl, or a pharmaceutically acceptable salt thereof.

12. A compound as claimed in claim 9, wherein $R_1$ is hydrogen and $R_2$ is $C_{2-3}$ alkanoyl or a pharmaceutically acceptable salt thereof.

13. A compound as claimed in claim 12, wherein $R_4$ is butylyl or isovaleryl or a pharmaceutically acceptable salt thereof.

14. A compound as claimed in claim 9, wherein $R_1$ and $R_2$ are hydrogen or a pharmaceutically acceptable salt thereof.

15. A compound as claimed in claim 14, wherein $R_4$ is butylyl or isovaleryl or a pharmaceutically acceptable salt thereof.

* * * * *